(12) United States Patent
Matsuzawa et al.

(10) Patent No.: US 9,517,002 B2
(45) Date of Patent: Dec. 13, 2016

(54) SOLID STATE IMAGE SENSOR, ENDOSCOPE, AND ENDOSCOPE SYSTEM

(71) Applicant: OLYMPUS CORPORATION, Tokyo (JP)

(72) Inventors: Hirohiko Matsuzawa, Hino (JP); Masahiro Kawauchi, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/140,552

(22) Filed: Apr. 28, 2016

(65) Prior Publication Data

US 2016/0235283 A1    Aug. 18, 2016

Related U.S. Application Data

(63) Continuation of application No. PCT/JP2015/058110, filed on Mar. 18, 2015.

(30) Foreign Application Priority Data

May 9, 2014    (JP) .................. 2014-097785

(51) Int. Cl.
*A61B 1/04* (2006.01)
*H04N 7/18* (2006.01)
(Continued)

(52) U.S. Cl.
CPC . *A61B 1/05* (2013.01); *A61B 1/00* (2013.01); *A61B 1/005* (2013.01);
(Continued)

(58) Field of Classification Search
CPC ... A61B 1/00; A61B 1/00009; A61B 1/00045; A61B 1/00096; A61B 1/005; A61B 1/04; A61B 1/05; A61B 1/0638; A61B 1/0661; A61B 1/07; G02B 23/24; H04N 5/335; H04N 9/07; H04N 9/045; H04N 2005/2255; H04N 2209/046; H04N 5/2254; H04N 2209/045; H04N 5/374; H01L 27/14645; G06T 3/4015; G06T 2207/10068; G06T 2207/10024; G06T 3/4007; G06T 3/4038; G06T 3/4023
See application file for complete search history.

(56) References Cited

U.S. PATENT DOCUMENTS 7,852,388 B2    12/2010    Shimizu et al.
8,111,286 B2    2/2012    Inuiya et al.
(Continued)

FOREIGN PATENT DOCUMENTS

JP    2005-334257 A    12/2005
JP    2007-054113 A    3/2007
(Continued)

OTHER PUBLICATIONS

International Search Report May 19, 2015 issued in PCT/JP2015/058110.
(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

A solid state image sensor includes: a light receiving unit where a plurality of photoelectric conversion elements storing charges according to a received light amount are arrayed; a reading unit configured to read an imaging signal based on the charges stored by the light receiving unit; and a color filter. The color filter includes filter units where each the red, green, and blue filters arrayed in four rows and four columns. The filter units are arrayed in a lattice shape. The filter unit is partitioned into read units. Each read unit includes two filters where each transmits light of the same wavelength band are adjacent to each other in one direction. The reading unit is configured to collectively read charges stored by two photoelectric conversion elements corresponding to the read unit.

8 Claims, 27 Drawing Sheets

(51) Int. Cl.
   *H04N 9/73*   (2006.01)
   *H04N 9/04*   (2006.01)
   *H04N 5/335*  (2011.01)
   *A61B 1/05*   (2006.01)
   *A61B 1/00*   (2006.01)
   *G02B 23/24*  (2006.01)
   *H04N 9/07*   (2006.01)
   *A61B 1/005*  (2006.01)
   *A61B 1/06*   (2006.01)
   *A61B 1/07*   (2006.01)
   *H04N 5/345*  (2011.01)
   *H04N 5/347*  (2011.01)
   *H04N 5/225*  (2006.01)

(52) U.S. Cl.
   CPC ...... *A61B 1/00009* (2013.01); *A61B 1/00045* (2013.01); *A61B 1/00096* (2013.01); *A61B 1/04* (2013.01); *A61B 1/0638* (2013.01); *A61B 1/0661* (2013.01); *A61B 1/07* (2013.01); *G02B 23/24* (2013.01); *H04N 5/335* (2013.01); *H04N 5/347* (2013.01); *H04N 5/3452* (2013.01); *H04N 9/04* (2013.01); *H04N 9/045* (2013.01); *H04N 9/07* (2013.01); *H04N 2005/2255* (2013.01)

(56) References Cited

U.S. PATENT DOCUMENTS

| | | | |
|---|---|---|---|
| 8,500,632 B2 | 8/2013 | Gono | |
| 8,764,634 B2* | 7/2014 | Matsuzawa | A61B 1/00013 600/109 |
| 8,908,022 B2* | 12/2014 | Ono | A61B 1/00009 348/45 |
| 9,250,121 B2* | 2/2016 | Tanaka | G02B 5/201 |
| 9,282,305 B2* | 3/2016 | Kikuchi | H04N 9/07 |
| 9,338,364 B2* | 5/2016 | Imade | G06T 3/4053 |
| 2005/0264687 A1 | 12/2005 | Murayama | |
| 2008/0267526 A1* | 10/2008 | Mitsunaga | H04N 5/35563 382/274 |
| 2013/0096380 A1* | 4/2013 | Matsuzawa | A61B 1/00013 600/109 |
| 2013/0169775 A1* | 7/2013 | Ono | A61B 1/00009 348/68 |
| 2013/0169843 A1* | 7/2013 | Ono | A61B 1/045 348/234 |
| 2013/0208101 A1* | 8/2013 | Ono | A61B 1/00193 348/65 |
| 2013/0286260 A1* | 10/2013 | Hirota | H04N 9/045 348/279 |
| 2014/0267390 A1* | 9/2014 | Padwick | G06T 11/00 345/629 |
| 2015/0109496 A1* | 4/2015 | Hirota | H04N 9/045 348/279 |
| 2015/0264325 A1* | 9/2015 | Hirota | H04N 9/045 348/279 |

FOREIGN PATENT DOCUMENTS

| | | |
|---|---|---|
| JP | 2007-317750 A | 12/2007 |
| JP | 2008-085807 A | 4/2008 |
| JP | 2012-005512 A | 1/2012 |
| JP | 2014-076375 A | 5/2014 |
| WO | WO 2007/010709 A1 | 1/2007 |

OTHER PUBLICATIONS

Japanese Office Action dated Oct. 13, 2015 issued in JP 2015-542508.

* cited by examiner

FIG.3

| $P_{11}$ | $P_{12}$ | $P_{13}$ | $P_{14}$ | $P_{15}$ | $P_{16}$ | $P_{17}$ | $P_{18}$ | ... |
|---|---|---|---|---|---|---|---|---|
| $P_{21}$ | $P_{22}$ | $P_{23}$ | $P_{24}$ | $P_{25}$ | $P_{26}$ | $P_{27}$ | $P_{28}$ | ... |
| $P_{31}$ | $P_{32}$ | $P_{33}$ | $P_{34}$ | $P_{35}$ | $P_{36}$ | $P_{37}$ | $P_{38}$ | ... |
| $P_{41}$ | $P_{42}$ | $P_{43}$ | $P_{44}$ | $P_{45}$ | $P_{46}$ | $P_{47}$ | $P_{48}$ | ... |
| $P_{51}$ | $P_{52}$ | $P_{53}$ | $P_{54}$ | $P_{55}$ | $P_{56}$ | $P_{57}$ | $P_{58}$ | ... |
| $P_{61}$ | $P_{62}$ | $P_{63}$ | $P_{64}$ | $P_{65}$ | $P_{66}$ | $P_{67}$ | $P_{68}$ | ... |
| $P_{71}$ | $P_{72}$ | $P_{73}$ | $P_{74}$ | $P_{75}$ | $P_{76}$ | $P_{77}$ | $P_{78}$ | ... |
| $P_{81}$ | $P_{82}$ | $P_{83}$ | $P_{84}$ | $P_{85}$ | $P_{86}$ | $P_{87}$ | $P_{88}$ | ... |
| ⋮ | ⋮ | ⋮ | ⋮ | ⋮ | ⋮ | ⋮ | ⋮ | ⋱ |

FIG.4

| | | C37 | C34 | | | | | |
|---|---|---|---|---|---|---|---|---|
| C11 C31 | C21 | C33 | C22 | C24 | | | | |
| $G_{11}$ | $G_{12}$ | $R_{13}$ | $R_{14}$ | $G_{15}$ | $G_{16}$ | $R_{17}$ | $R_{18}$ | ... |
| $B_{21}$ | $B_{22}$ | $B_{23}$ | $B_{24}$ | $B_{25}$ | $B_{26}$ | $B_{27}$ | $B_{28}$ | ... |
| $G_{31}$ | $G_{32}$ | $G_{33}$ | $G_{34}$ | $G_{35}$ | $G_{36}$ | $G_{37}$ | $G_{38}$ | ... |
| $B_{41}$ | $B_{42}$ | $B_{43}$ | $B_{44}$ | $B_{45}$ | $B_{46}$ | $B_{47}$ | $B_{48}$ | ... |
| $G_{51}$ | $G_{52}$ | $R_{53}$ | $R_{54}$ | $G_{55}$ | $G_{56}$ | $R_{57}$ | $R_{58}$ | ... |
| $B_{61}$ | $B_{62}$ | $B_{63}$ | $B_{64}$ | $B_{65}$ | $B_{66}$ | $B_{67}$ | $B_{68}$ | ... |
| $G_{71}$ | $G_{72}$ | $G_{73}$ | $G_{74}$ | $G_{75}$ | $G_{76}$ | $G_{77}$ | $G_{78}$ | ... |
| $B_{81}$ | $B_{82}$ | $B_{83}$ | $B_{84}$ | $B_{85}$ | $B_{86}$ | $B_{87}$ | $B_{88}$ | ... |
| ⋮ | ⋮ | ⋮ | ⋮ | ⋮ | ⋮ | ⋮ | ⋮ | ⋱ |

| G$_{11}$ | G$_{12}$ | R$_{13}$ | R$_{14}$ | G$_{15}$ | G$_{16}$ | R$_{17}$ | R$_{18}$ | ... |
|---|---|---|---|---|---|---|---|---|
| B$_{21}$ | B$_{22}$ | B$_{23}$ | B$_{24}$ | B$_{25}$ | B$_{26}$ | B$_{27}$ | B$_{28}$ | ... |
| G$_{31}$ | G$_{32}$ | G$_{33}$ | G$_{34}$ | G$_{35}$ | G$_{36}$ | G$_{37}$ | G$_{38}$ | ... |
| B$_{41}$ | B$_{42}$ | B$_{43}$ | B$_{44}$ | B$_{45}$ | B$_{46}$ | B$_{47}$ | B$_{48}$ | ... |
| G$_{51}$ | G$_{52}$ | R$_{53}$ | R$_{54}$ | G$_{55}$ | G$_{56}$ | R$_{57}$ | R$_{58}$ | ... |
| B$_{61}$ | B$_{62}$ | B$_{63}$ | B$_{64}$ | B$_{65}$ | B$_{66}$ | B$_{67}$ | B$_{68}$ | ... |
| G$_{71}$ | G$_{72}$ | G$_{73}$ | G$_{74}$ | G$_{75}$ | G$_{76}$ | G$_{77}$ | G$_{78}$ | ... |
| B$_{81}$ | B$_{82}$ | B$_{83}$ | B$_{84}$ | B$_{85}$ | B$_{86}$ | B$_{87}$ | B$_{88}$ | ... |
| ⋮ | ⋮ | ⋮ | ⋮ | ⋮ | ⋮ | ⋮ | ⋮ | ⋱ |

FIG.7

| $G_{11}$ | $G_{12}$ | $R_{13}$ | $R_{14}$ | $G_{15}$ | $G_{16}$ | $R_{17}$ | $R_{18}$ | ... |
|---|---|---|---|---|---|---|---|---|
| $B_{21}$ | $B_{22}$ | $B_{23}$ | $B_{24}$ | $B_{25}$ | $B_{26}$ | $B_{27}$ | $B_{28}$ | ... |
| $G_{31}$ | $G_{32}$ | $G_{33}$ | $G_{34}$ | $G_{35}$ | $G_{36}$ | $G_{37}$ | $G_{38}$ | ... |
| $B_{41}$ | $B_{42}$ | $B_{43}$ | $B_{44}$ | $B_{45}$ | $B_{46}$ | $B_{47}$ | $B_{48}$ | ... |
| $G_{51}$ | $G_{52}$ | $R_{53}$ | $R_{54}$ | $G_{55}$ | $G_{56}$ | $R_{57}$ | $R_{58}$ | ... |
| $B_{61}$ | $B_{62}$ | $B_{63}$ | $B_{64}$ | $B_{65}$ | $B_{66}$ | $B_{67}$ | $B_{68}$ | ... |
| $G_{71}$ | $G_{72}$ | $G_{73}$ | $G_{74}$ | $G_{75}$ | $G_{76}$ | $G_{77}$ | $G_{78}$ | ... |
| $B_{81}$ | $B_{82}$ | $B_{83}$ | $B_{84}$ | $B_{85}$ | $B_{86}$ | $B_{87}$ | $B_{88}$ | ... |
| ⋮ | ⋮ | ⋮ | ⋮ | ⋮ | ⋮ | ⋮ | ⋮ | ⋱ |

FIG.8

| $G_{11}$ | $G_{12}$ | $R_{13}$ | $R_{14}$ | $G_{15}$ | $G_{16}$ | $R_{17}$ | $R_{18}$ | ... |
|---|---|---|---|---|---|---|---|---|
| $B_{21}$ | $B_{22}$ | $B_{23}$ | $B_{24}$ | $B_{25}$ | $B_{26}$ | $B_{27}$ | $B_{28}$ | ... |
| $G_{31}$ | $G_{32}$ | $G_{33}$ | $G_{34}$ | $G_{35}$ | $G_{36}$ | $G_{37}$ | $G_{38}$ | ... |
| $B_{41}$ | $B_{42}$ | $B_{43}$ | $B_{44}$ | $B_{45}$ | $B_{46}$ | $B_{47}$ | $B_{48}$ | ... |
| $G_{51}$ | $G_{52}$ | $R_{53}$ | $R_{54}$ | $G_{55}$ | $G_{56}$ | $R_{57}$ | $R_{58}$ | ... |
| $B_{61}$ | $B_{62}$ | $B_{63}$ | $B_{64}$ | $B_{65}$ | $B_{66}$ | $B_{67}$ | $B_{68}$ | ... |
| $G_{71}$ | $G_{72}$ | $G_{73}$ | $G_{74}$ | $G_{75}$ | $G_{76}$ | $G_{77}$ | $G_{78}$ | ... |
| $B_{81}$ | $B_{82}$ | $B_{83}$ | $B_{84}$ | $B_{85}$ | $B_{86}$ | $B_{87}$ | $B_{88}$ | ... |
| ⋮ | ⋮ | ⋮ | ⋮ | ⋮ | ⋮ | ⋮ | ⋮ | ⋱ |

FIG.9

|  $S_{11}$ | $S_{12}$ | $S_{13}$ | $S_{14}$ | ... |
|---|---|---|---|---|
| $S_{21}$ | $S_{22}$ | $S_{23}$ | $S_{24}$ | ... |
| $S_{31}$ | $S_{32}$ | $S_{33}$ | $S_{34}$ | ... |
| $S_{41}$ | $S_{42}$ | $S_{43}$ | $S_{44}$ | ... |
| ⋮ | ⋮ | ⋮ | ⋮ | ⋱ |

FIG.12

|  |  |  |  |  |
|---|---|---|---|---|
| $Bs_{11}$ | $Bs_{12}$ | $Bs_{13}$ | $Bs_{14}$ | ... |
| $Bs_{21}$ | $Bs_{22}$ | $Bs_{23}$ | $Bs_{24}$ | ... |
| $Bs_{31}$ | $Bs_{32}$ | $Bs_{33}$ | $Bs_{34}$ | ... |
| $Bs_{41}$ | $Bs_{42}$ | $Bs_{43}$ | $Bs_{44}$ | ... |
| ⋮ | ⋮ | ⋮ | ⋮ | ⋱ |

FIG.13

|   |   |   |   |   |   |   |   |   |
|---|---|---|---|---|---|---|---|---|
| $B_{11}$ | $B_{12}$ | $R_{13}$ | $R_{14}$ | $B_{15}$ | $B_{16}$ | $R_{17}$ | $R_{18}$ | ... |
| $G_{21}$ | $G_{22}$ | $G_{23}$ | $G_{24}$ | $G_{25}$ | $G_{26}$ | $G_{27}$ | $G_{28}$ | ... |
| $B_{31}$ | $B_{32}$ | $B_{33}$ | $B_{34}$ | $B_{35}$ | $B_{36}$ | $B_{37}$ | $B_{38}$ | ... |
| $G_{41}$ | $G_{42}$ | $G_{43}$ | $G_{44}$ | $G_{45}$ | $G_{46}$ | $G_{47}$ | $G_{48}$ | ... |
| $B_{51}$ | $B_{52}$ | $R_{53}$ | $R_{54}$ | $B_{55}$ | $B_{56}$ | $R_{57}$ | $R_{58}$ | ... |
| $G_{61}$ | $G_{62}$ | $G_{63}$ | $G_{64}$ | $G_{65}$ | $G_{66}$ | $G_{67}$ | $G_{68}$ | ... |
| $B_{71}$ | $B_{72}$ | $B_{73}$ | $B_{74}$ | $B_{75}$ | $B_{76}$ | $B_{77}$ | $B_{78}$ | ... |
| $G_{81}$ | $G_{82}$ | $G_{83}$ | $G_{84}$ | $G_{85}$ | $G_{86}$ | $G_{87}$ | $G_{88}$ | ... |
| : | : | : | : | : | : | : | : | ∴ |

Labels: C11a, C31a, C21a, C33a, C37a, C22a, C34a, C24a, C32a, C35a, C23a, C36a, C38a

FIG.15

| | | C37b C34b | | | | | |
|---|---|---|---|---|---|---|---|
| C11b C31b C21b C33b C22b C24b | | | | | | | |

| G₁₁ | G₁₂ | R₁₃ | R₁₄ | G₁₅ | G₁₆ | R₁₇ | R₁₈ | ... |
|---|---|---|---|---|---|---|---|---|
| B₂₁ | B₂₂ | G₂₃ | G₂₄ | B₂₅ | B₂₆ | G₂₇ | G₂₈ | ... |
| B₃₁ | B₃₂ | G₃₃ | G₃₄ | B₃₅ | B₃₆ | G₃₇ | G₃₈ | ... |
| G₄₁ | G₄₂ | B₄₃ | B₄₄ | G₄₅ | G₄₆ | B₄₇ | B₄₈ | ... |
| G₅₁ | G₅₂ | R₅₃ | R₅₄ | G₅₅ | G₅₆ | R₅₇ | R₅₈ | ... |
| B₆₁ | B₆₂ | G₆₃ | G₆₄ | B₆₅ | B₆₆ | G₆₇ | G₆₈ | ... |
| B₇₁ | B₇₂ | G₇₃ | G₇₄ | B₇₅ | B₇₆ | G₇₇ | G₇₈ | ... |
| G₈₁ | G₈₂ | B₈₃ | B₈₄ | G₈₅ | G₈₆ | B₈₇ | B₈₈ | ... |

| $G_{11}$ | $G_{12}$ | $R_{13}$ | $R_{14}$ | $G_{15}$ | $G_{16}$ | $R_{17}$ | $R_{18}$ | ... |
|---|---|---|---|---|---|---|---|---|
| $B_{21}$ | $B_{22}$ | $G_{23}$ | $G_{24}$ | $B_{25}$ | $B_{26}$ | $G_{27}$ | $G_{28}$ | ... |
| $B_{31}$ | $B_{32}$ | $G_{33}$ | $G_{34}$ | $B_{35}$ | $B_{36}$ | $G_{37}$ | $G_{38}$ | ... |
| $G_{41}$ | $G_{42}$ | $B_{43}$ | $B_{44}$ | $G_{45}$ | $G_{46}$ | $B_{47}$ | $B_{48}$ | ... |
| $G_{51}$ | $G_{52}$ | $R_{53}$ | $R_{54}$ | $G_{55}$ | $G_{56}$ | $R_{57}$ | $R_{58}$ | ... |
| $B_{61}$ | $B_{62}$ | $G_{63}$ | $G_{64}$ | $B_{65}$ | $B_{66}$ | $G_{67}$ | $G_{68}$ | ... |
| $B_{71}$ | $B_{72}$ | $G_{73}$ | $G_{74}$ | $B_{75}$ | $B_{76}$ | $G_{77}$ | $G_{78}$ | ... |
| $G_{81}$ | $G_{82}$ | $B_{83}$ | $B_{84}$ | $G_{85}$ | $G_{86}$ | $B_{87}$ | $B_{88}$ | ... |
| ⋮ | ⋮ | ⋮ | ⋮ | ⋮ | ⋮ | ⋮ | ⋮ | ⋱ |

| $G_{11}$ | $G_{12}$ | $R_{13}$ | $R_{14}$ | $G_{15}$ | $G_{16}$ | $R_{17}$ | $R_{18}$ | ⋯ |
|---|---|---|---|---|---|---|---|---|
| $B_{11}$ | $B_{22}$ | $G_{23}$ | $G_{24}$ | $B_{25}$ | $B_{26}$ | $G_{27}$ | $G_{28}$ | ⋯ |
| $B_{31}$ | $B_{32}$ | $G_{33}$ | $G_{34}$ | $B_{35}$ | $B_{36}$ | $G_{37}$ | $G_{38}$ | ⋯ |
| $G_{41}$ | $G_{42}$ | $B_{43}$ | $B_{44}$ | $G_{45}$ | $G_{46}$ | $B_{47}$ | $B_{48}$ | ⋯ |
| $G_{51}$ | $G_{52}$ | $R_{53}$ | $R_{54}$ | $G_{55}$ | $G_{56}$ | $R_{57}$ | $R_{58}$ | ⋯ |
| $B_{61}$ | $B_{62}$ | $G_{63}$ | $G_{64}$ | $B_{65}$ | $B_{66}$ | $G_{67}$ | $G_{68}$ | ⋯ |
| $B_{71}$ | $B_{72}$ | $G_{73}$ | $G_{74}$ | $B_{75}$ | $B_{76}$ | $G_{77}$ | $G_{78}$ | ⋯ |
| $G_{81}$ | $G_{82}$ | $B_{83}$ | $B_{84}$ | $G_{85}$ | $G_{86}$ | $B_{87}$ | $B_{88}$ | ⋯ |
| ⋮ | ⋮ | ⋮ | ⋮ | ⋮ | ⋮ | ⋮ | ⋮ | ⋱ |

FIG.24

|  | C11c | | C37c C34c | | | | | |
|---|---|---|---|---|---|---|---|---|
|  | C31c | C21c C33c | C22c | C24c | | | | |
|  | $B_{11}$ | $B_{12}$ | $R_{13}$ | $R_{14}$ | $B_{15}$ | $B_{16}$ | $R_{17}$ | $R_{18}$ | ... |
| C32c | $G_{21}$ | $G_{22}$ | $B_{23}$ | $B_{24}$ | $G_{25}$ | $G_{26}$ | $B_{27}$ | $B_{28}$ | ... |
| C35c C23c | $B_{31}$ | $B_{32}$ | $G_{33}$ | $G_{34}$ | $B_{35}$ | $B_{36}$ | $G_{37}$ | $G_{38}$ | ... |
| C36c | $G_{41}$ | $G_{42}$ | $B_{43}$ | $B_{44}$ | $G_{45}$ | $G_{46}$ | $B_{47}$ | $B_{48}$ | ... |
| C38c | $B_{51}$ | $B_{52}$ | $R_{53}$ | $R_{54}$ | $B_{55}$ | $B_{56}$ | $R_{57}$ | $R_{58}$ | ... |
|  | $G_{61}$ | $G_{62}$ | $B_{63}$ | $B_{64}$ | $G_{65}$ | $G_{66}$ | $B_{67}$ | $B_{68}$ | ... |
|  | $B_{71}$ | $B_{72}$ | $G_{73}$ | $G_{74}$ | $B_{75}$ | $B_{76}$ | $G_{77}$ | $G_{78}$ | ... |
|  | $G_{81}$ | $G_{82}$ | $B_{83}$ | $B_{84}$ | $G_{85}$ | $G_{86}$ | $B_{87}$ | $B_{88}$ | ... |
|  | : | : | : | : | : | : | : | : | ⋱ |

FIG.25

|  | $G_{11}$ | $G_{12}$ | $R_{13}$ | $R_{14}$ | $G_{15}$ | $G_{16}$ | $R_{17}$ | $R_{18}$ | ... |
|---|---|---|---|---|---|---|---|---|---|
|  | $B_{21}$ | $B_{22}$ | $G_{23}$ | $G_{24}$ | $B_{25}$ | $B_{26}$ | $G_{27}$ | $G_{28}$ | ... |
|  | $G_{31}$ | $G_{32}$ | $B_{33}$ | $B_{34}$ | $G_{35}$ | $G_{36}$ | $B_{37}$ | $B_{38}$ | ... |
|  | $B_{41}$ | $B_{42}$ | $G_{43}$ | $G_{44}$ | $B_{45}$ | $B_{46}$ | $G_{47}$ | $G_{48}$ | ... |
|  | $G_{51}$ | $G_{52}$ | $R_{53}$ | $R_{54}$ | $G_{55}$ | $G_{56}$ | $R_{57}$ | $R_{58}$ | ... |
|  | $B_{61}$ | $B_{62}$ | $G_{63}$ | $G_{64}$ | $B_{65}$ | $B_{66}$ | $G_{67}$ | $G_{68}$ | ... |
|  | $G_{71}$ | $G_{72}$ | $B_{73}$ | $B_{74}$ | $G_{75}$ | $G_{76}$ | $B_{77}$ | $B_{78}$ | ... |
|  | $B_{81}$ | $B_{82}$ | $G_{83}$ | $G_{84}$ | $B_{85}$ | $B_{86}$ | $G_{87}$ | $G_{88}$ | ... |

FIG.26

|  | | | | | | | | |
|---|---|---|---|---|---|---|---|---|
| $G_{11}$ | $G_{12}$ | $R_{13}$ | $R_{14}$ | $G_{15}$ | $G_{16}$ | $R_{17}$ | $R_{18}$ | ... |
| $B_{21}$ | $B_{22}$ | $G_{23}$ | $G_{24}$ | $B_{25}$ | $B_{26}$ | $G_{27}$ | $G_{28}$ | ... |
| $R_{31}$ | $R_{32}$ | $B_{33}$ | $B_{34}$ | $R_{35}$ | $R_{36}$ | $B_{37}$ | $B_{38}$ | ... |
| $B_{41}$ | $B_{42}$ | $G_{43}$ | $G_{44}$ | $B_{45}$ | $B_{46}$ | $G_{47}$ | $G_{48}$ | ... |
| $G_{51}$ | $G_{52}$ | $R_{53}$ | $R_{54}$ | $G_{55}$ | $G_{56}$ | $R_{57}$ | $R_{58}$ | ... |
| $B_{61}$ | $B_{62}$ | $G_{63}$ | $G_{64}$ | $B_{65}$ | $B_{66}$ | $G_{67}$ | $G_{68}$ | ... |
| $R_{71}$ | $R_{72}$ | $B_{73}$ | $B_{74}$ | $R_{75}$ | $R_{76}$ | $B_{77}$ | $B_{78}$ | ... |
| $B_{81}$ | $B_{82}$ | $G_{83}$ | $G_{84}$ | $B_{85}$ | $B_{86}$ | $G_{87}$ | $G_{88}$ | ... |
| ⋮ | ⋮ | ⋮ | ⋮ | ⋮ | ⋮ | ⋮ | ⋮ | ⋱ |

FIG.27

|  | C11f | C21f | C32f | C33f | C38f | C34f | C22f | C24f |  |  |  |
|---|---|---|---|---|---|---|---|---|---|---|---|
|  | G₁₁ | B₁₂ | B₁₃ | G₁₄ | G₁₅ | B₁₆ | B₁₇ | G₁₈ | ... |
| C31f | G₂₁ | B₂₂ | B₂₃ | G₂₄ | G₂₅ | B₂₆ | B₂₇ | G₂₈ | ... |
| C35f / C23f | R₃₁ | G₃₂ | G₃₃ | B₃₄ | R₃₅ | G₃₆ | G₃₇ | B₃₈ | ... |
|  | R₄₁ | G₄₂ | G₄₃ | B₄₄ | R₄₅ | G₄₆ | G₄₇ | B₄₈ | ... |
| C36f / C37f | G₅₁ | B₅₂ | B₅₃ | G₅₄ | G₅₅ | B₅₆ | B₅₇ | G₅₈ | ... |
|  | G₆₁ | B₆₂ | B₆₃ | G₆₄ | G₆₅ | B₆₆ | B₆₇ | G₆₈ | ... |
|  | R₇₁ | G₇₂ | G₇₃ | B₇₄ | R₇₅ | G₇₆ | G₇₇ | B₇₈ | ... |
|  | R₈₁ | G₈₂ | G₈₃ | B₈₄ | R₈₅ | G₈₆ | G₈₇ | B₈₈ | ... |
|  | ⋮ | ⋮ | ⋮ | ⋮ | ⋮ | ⋮ | ⋮ | ⋮ | ⋱ |

SOLID STATE IMAGE SENSOR, ENDOSCOPE, AND ENDOSCOPE SYSTEM

CROSS REFERENCES TO RELATED APPLICATIONS

This application is a continuation of PCT international application Ser. No. PCT/JP2015/058110, filed on Mar. 18, 2015 which designates the United States, incorporated herein by reference, and which claims the benefit of priority from Japanese Patent Applications No. 2014-097785, filed on May 9, 2014, incorporated herein by reference.

BACKGROUND

1. Technical Field

The disclosure relates to a solid state image sensor generating an imaging signal by photoelectric conversion of light and an endoscope and an endoscope system acquiring the imaging signal generated by the solid state image sensor.

2. Related Art

In the related art, endoscopes are widely used for various examinations in medical fields and industrial fields. Among them, in medical endoscopes, a flexible insertion unit having an elongated shape where an imaging element including a plurality of pixels is provided to a distal end thereof is inserted into a body cavity of an subject such as a patient, and thus, an in-vivo image of an inner portion of the body cavity can be acquired without cutting the subject. Therefore, small burden is exerted on the subject, and the spread is proceeding.

As imaging modes of the endoscope, there are widely known a white light imaging (WLI) mode using white illumination light and a narrow-band imaging (NBI) mode using illumination light (narrow-band illumination light) including light of two narrow bands included in each of wavelength bands of, for example, blue light and green light. Among them, in the narrow-band imaging mode, an image for highlighting capillaries existing on a biological mucosal surface (biological surface), mucosal fine patterns, and the like can be obtained. According to the narrow-band imaging mode, a lesion on the biological mucosal surface can be more accurately identified. In the endoscope, it is preferable that observation be performed by switching between the white light imaging mode and the narrow-band imaging mode.

In the above-described imaging mode, since a color image is generated to be displayed, in order to acquire an image captured by a single plate with a solid state image sensor, in general, color filters arrayed for respective pixels using a filter array called a Bayer array as one unit are provided on a light receiving plane of the solid state image sensor (for example, refer to Japanese Laid-open Patent Publication No. 2005-334257). In this case, each pixel receives light of a wavelength band passing through the filter and generates an electric signal of a color component according to the light of the wavelength band. For this reason, in a process of generating the color image, an interpolation process is performed to interpolate a signal value of a missing color component which does not pass through the filter corresponding to each pixel.

Japanese Laid-open Patent Publication No. 2007-54113 discloses an array of color filters for performing observation appropriate to the narrow-band imaging mode. According to Japanese Laid-open Patent Publication No. 2007-54113, since one of two filters transmitting light of a green wavelength band in a Bayer array is replaced with a filter transmitting light of a blue wavelength band, the image obtained in the narrow-band imaging mode can be clarified.

SUMMARY

In some embodiments, a solid state image sensor includes: a light receiving unit where a plurality of photoelectric conversion elements storing charges according to a received light amount are arrayed in a lattice shape; a reading unit configured to read an imaging signal based on the charges stored by the light receiving unit; and a color filter including: red filters where each transmits light of a red wavelength band; green filters where each transmits light of a green wavelength band; and blue filters where each transmits light of a blue wavelength band, each of the red, green, and blue filters being disposed at a position corresponding to any one of the plurality of photoelectric conversion elements on a light receiving plane of the light receiving unit. The color filter includes filter units where each includes the red, green, and blue filters arrayed in four rows and four columns. The filter units are arrayed in a lattice shape. The filter unit is set so that a total number of the green filters is six or more and eight or less, a total number of the blue filters is six or more and eight or less, a total number of the red filters is two or more and four or less, and a total number of the red, green, and blue filters is sixteen. The filter unit is partitioned into read units. Each read unit includes two filters where each transmits light of the same wavelength band. The two filters are adjacent to each other in one direction. The reading unit is configured to collectively read charges stored by two photoelectric conversion elements corresponding to the read unit.

In some embodiments, an endoscope includes the solid state image sensor at a distal end of an insertion unit of the endoscope.

In some embodiments, an endoscope system includes: an endoscope provided with the solid state image sensor at a distal end of an insertion unit of the endoscope; an illumination unit configured to emit white illumination light including light of red, green, and blue wavelength bands or narrow-band illumination light including: light of a narrow band included in the blue wavelength band; and light of a narrow band included in the green wavelength band; and an image processing unit connected to the endoscope and configured to generate an image signal for image display based on the imaging signal obtained from the endoscope. The filter unit is partitioned into basic units, each basic unit where four filters corresponding to two read units adjacent to each other in a direction perpendicular to the one direction are arrayed in two rows and two columns. The image processing unit is configured: to generate image information of a single color component for every color component using the basic unit as a unit based on signal values of the photoelectric conversion elements corresponding to the read unit; and to generate an image signal for image display based on the generated image information.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3 is a schematic diagram illustrating a configuration of a sensor unit according to the first embodiment of the disclosure;

FIG. 4 is a schematic diagram illustrating an example of a configuration of a color filter according to the first embodiment of the disclosure;

FIG. 6 is a diagram explaining a color component acquisition mode of the sensor unit according to the first embodiment of the disclosure and is a diagram explaining acquisition of a red component from R pixels;

FIG. 7 is a diagram explaining a color component acquisition mode of the sensor unit according to the first embodiment of the disclosure and is a diagram explaining acquisition of a green component from G pixels;

FIG. 8 is a diagram explaining a color component acquisition mode of the sensor unit according to the first embodiment of the disclosure and is a diagram explaining acquisition of a blue component from B pixels;

FIG. 9 is a diagram explaining an extraction process of an extraction unit according to the first embodiment of the disclosure and is a diagram explaining an extraction area;

FIG. 12 is a diagram explaining an extraction process of the extraction unit according to the first embodiment of the disclosure and is a diagram illustrating an extraction image with respect to a blue component;

FIG. 13 is a schematic diagram illustrating an example of a configuration of a color filter according to a modified example of the first embodiment of the disclosure;

FIG. 15 is a schematic diagram illustrating an example of a configuration of a color filter according to the second embodiment of the disclosure;

FIG. 17 is a diagram explaining a charge reading mode of a sensor unit according to the second embodiment of the disclosure and is a diagram explaining reading of the pixels of odd-numbered rows;

FIG. 18 is a diagram explaining an extraction process of an extraction unit according to the second embodiment of the disclosure and is a diagram illustrating an extraction image with respect to a red component;

FIG. 20 is a diagram explaining an extraction process of the extraction unit according to the second embodiment of the disclosure and is a diagram illustrating an extraction image with respect to a blue component;

FIG. 21 is a diagram explaining a charge reading mode of the sensor unit according to the second embodiment of the disclosure and is a diagram explaining reading of the pixels of even-numbered rows;

FIG. 24 is a schematic diagram illustrating an example of a configuration of a color filter according to Modified Example 1 of the second embodiment of the disclosure;

FIG. 25 is a schematic diagram illustrating an example of a configuration of a color filter according to Modified Example 2 of the second embodiment of the disclosure;

FIG. 26 is a schematic diagram illustrating an example of a configuration of a color filter according to Modified Example 3 of the second embodiment of the disclosure; and FIG. 27 is a schematic diagram illustrating an example of a configuration of a color filter according to a third embodiment of the disclosure.

DETAILED DESCRIPTION

Hereinafter, modes (hereinafter, referred to as "embodiments") for embodying the present invention will be described. In the embodiments, a medical endoscope system capturing and displaying an in-vivo image of a subject such as a patient will be described. In addition, the present invention is not limited to the embodiments. In the description with respect to the drawings, the same components are denoted by the same reference signs.

First Embodiment

Figure 1:
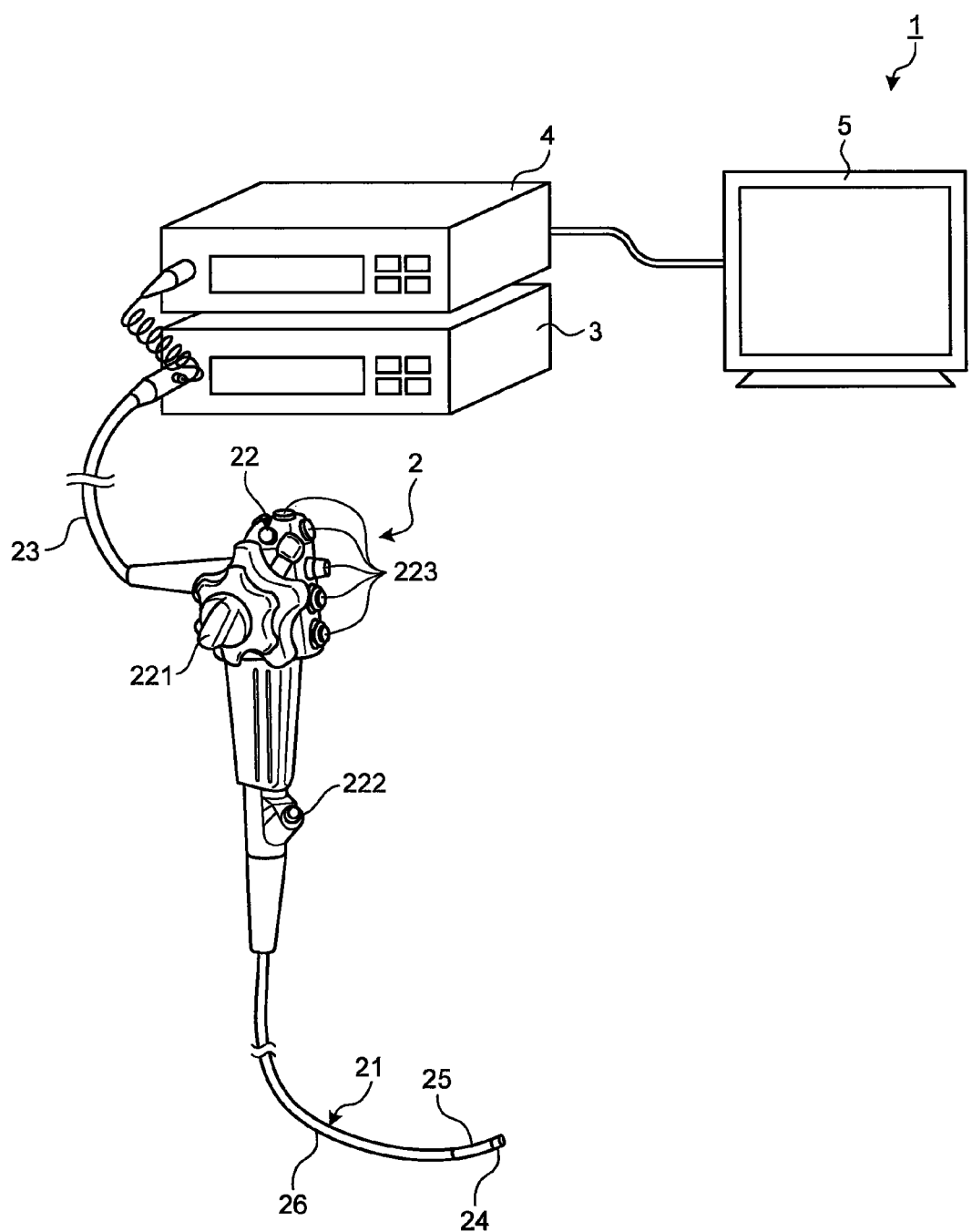
FIG. 1 is a diagram illustrating a schematic configuration of an endoscope system according to a first embodiment of the disclosure.
Figure 2:
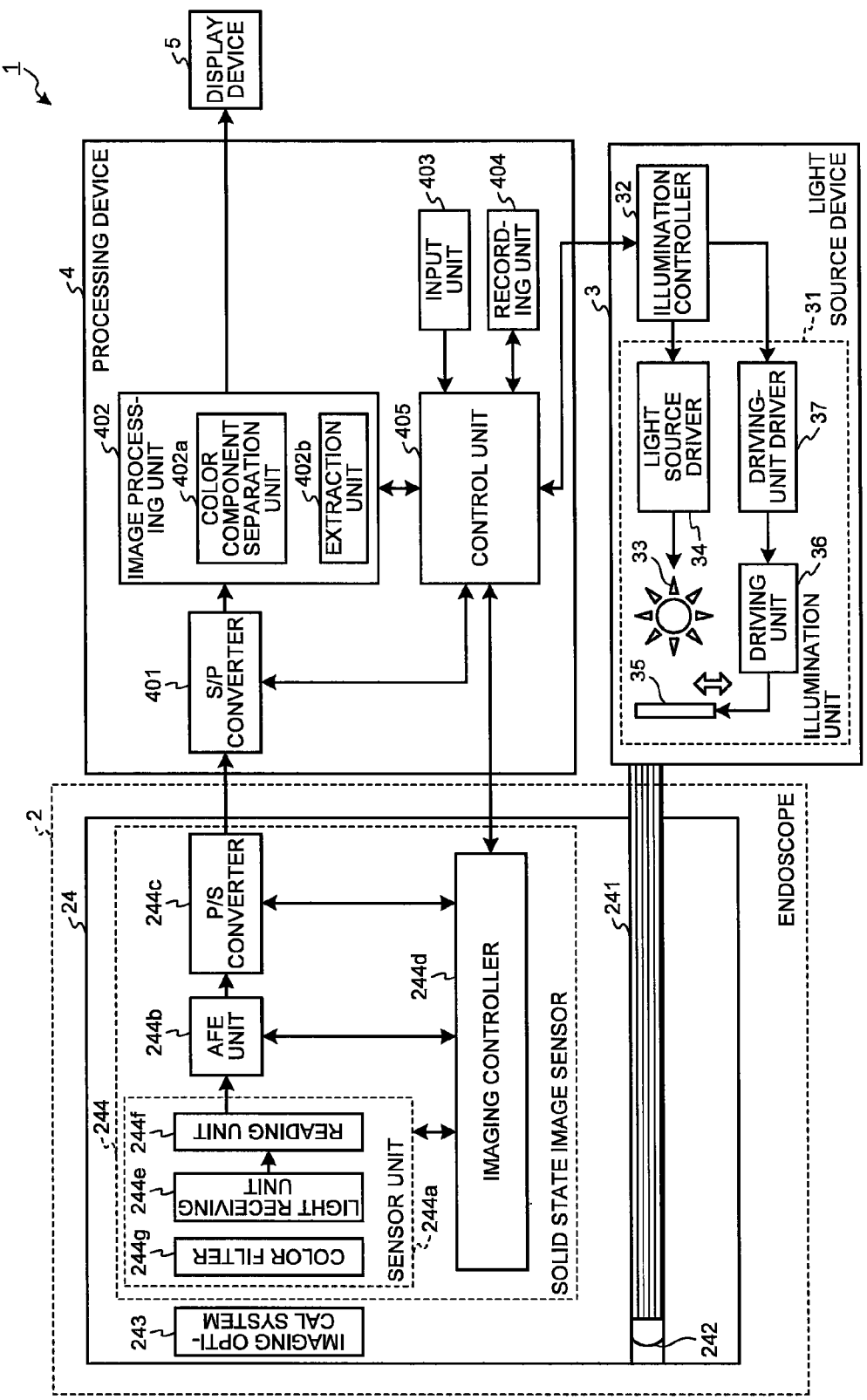
FIG. 2 is a block diagram illustrating the schematic configuration of the endoscope system according to the first embodiment of the disclosure.

FIG. 1 is a diagram illustrating a schematic configuration of an endoscope system according a first embodiment of the disclosure. FIG. 2 is a block diagram illustrating the schematic configuration of the endoscope system according to the first embodiment.

An endoscope system 1 illustrated in FIGS. 1 and 2 includes an endoscope 2 which acquires an in-vivo image of a subject by inserting a distal end portion thereof into a body cavity of the subject, a light source device 3 which generates illumination light which is to be emitted from the distal end of the endoscope 2, a processing device 4 which performs a predetermined image process on the in-vivo image acquired by the endoscope 2 and controls overall operations of the endoscope system 1, and a display device 5 which displays the in-vivo image which is image-processed by the processing device 4.

The endoscope 2 includes an insertion unit 21 which has flexibility and is formed in an elongated shape, an operating unit 22 which is connected to a base end side of the insertion unit 21 and receives input of various operating signals, and a universal cord 23, which is extended from the operating unit 22 in a direction different from an extension direction of the insertion unit 21, is detachable from the light source device 3 and the processing device 4, and incorporates various cables which are to be electrically connected to the light source device 3 and the processing device 4.

The insertion unit 21 includes a distal end portion 24 incorporating a solid state image sensor 244 where pixels generating an electric signal (imaging signal) by receiving light and performing photoelectric conversion are arrayed in a two-dimensional shape, a bendable bending portion 25 configured with a plurality of bending pieces, and a flexible tube portion 26 having flexibility and being in an elongated shape which is connected to a base end side of the bending portion 25. As the solid state image sensor 244 provided to the distal end portion 24, for example, there is a CMOS image sensor.

The distal end portion 24 includes a light guide 241, an illumination lens 242, an imaging optical system 243 (objective optical system), and the solid state image sensor 244.

The light guide 241 is configured with a glass fiber or the like to form a light guide path of the light emitted by the light source device 3.

The illumination lens 242 is provided to a distal end of the light guide 241 and emits light from the light guide 241 to the outside.

The imaging optical system 243 is provided between a distal end surface of the distal end portion 24 and a color filter 244g and is configured with one lens or a plurality of lenses.

The solid state image sensor 244 generates the imaging signal by performing photoelectric conversion on the light received through the imaging optical system 243 and performs parallel/serial conversion on a digitalized imaging signal to output the signal. The solid state image sensor 244 includes a sensor unit 244a, an analog front end unit 244b (hereinafter, referred to as an "AFE unit 244b"), a P/S converter 244c, and an imaging controller 244d.

The sensor unit 244a includes a light receiving unit 244e, a reading unit 244f, and a color filter 244g.

In the light receiving unit 244e, a plurality of pixels (photoelectric conversion elements), each of which includes a photodiode storing charges according to a light amount and an amplifier amplifying the charges stored by the photodiode are arrayed in a lattice (matrix) shape, and the charges generated through the photoelectric conversion are stored.

The reading unit 244f reads an imaging signal according to the charges stored by the plurality of pixels of the light receiving unit 244e and outputs the imaging signal to the AFE unit 244b.

The color filter 244g includes a plurality of filters which are provided on a light receiving plane of the light receiving unit 244e and each filter passes light of respective wavelength bands individually set.

FIG. 3 is a schematic diagram illustrating a configuration of the sensor unit according to the first embodiment. In the light receiving unit 244e, the plurality of pixels receiving light from the outside are arrayed in a matrix shape. In the light receiving unit 244e, each pixel stores charges by performing photoelectric conversion on the received light. The charges stored in each pixel are converted into a voltage to be read as the imaging signal by the reading unit 244f. The imaging signal includes a pixel value (luminance value) of each pixel, position information of the pixel, and the like. In FIG. 3, a pixel disposed at the i-th row and the j-th column is denoted as a pixel $P_{ij}$.

FIG. 4 is a schematic diagram illustrating an example of a configuration of the color filter according to the first embodiment. In the first embodiment, the color filter 244g includes filter units C11 disposed to be aligned two-dimensionally (in a matrix shape) according to the array of the pixels $P_{ij}$. Each filter unit C11 is configured with sixteen filters aligned in a 4×4 matrix shape. The pixel $P_{ij}$ provided with the filter receives light of a wavelength band which is transmitted by the filter. For example, the pixel $P_{ij}$ provided with the filter transmitting light of a blue wavelength band receives light of the blue wavelength band. Hereinafter, the pixel $P_{ij}$ receiving the light of the blue wavelength band is referred to as a B pixel. Similarly, the pixel receiving the light of the green wavelength band is referred to as a G pixel, and the pixel receiving the light of the red wavelength band is referred to as an R pixel.

The filter unit C11 is partitioned into basic units C21 to C24 which are four areas divided in 2 rows×2 columns. In addition, the basic units C21 to C24 are partitioned into read units C31 to C38 which are formed by dividing each basic unit in 1 row×2 columns. More specifically, the basic unit C21 is divided in 1 row×2 columns to include the read units C31 and C32, the basic unit C22 is divided in 1 row×2 columns to include the read units C33 and C34, the basic unit C23 is divided in 1 row×2 columns to include the read units C35 and C36, and the basic unit C24 is divided in 1 row×2 columns to include the read units C37 and C38.

The filter unit C11 transmits the light of the blue (B) wavelength band $H_B$, the light of the green (G) wavelength band $H_G$, and the light of the red (R) wavelength band $H_R$. In addition, in the filter unit C11, the plurality of filters are selected among the sixteen filters to be disposed so that the number of filters transmitting the light of the wavelength band $H_G$ is six or more, the number of filters transmitting the light of the wavelength band $H_B$ is six or more, and the number of filters transmitting the light of the wavelength band $H_R$ is two or more and four or less. With respect to the blue, green, and read wavelength bands $H_B$, $H_G$, and $H_R$, for example, the wavelength band $H_B$ is 390 nm to 500 nm, the wavelength band $H_G$ is 500 nm to 600 nm, and the wavelength band $H_R$ is 600 nm to 700 nm.

As illustrated in FIG. 4, the filter unit C11 according to the first embodiment is configured with the six (6/16) G filters transmitting the light of the wavelength band $H_G$, the eight (8/16) B filters transmitting the light of the wavelength band $H_B$, and the two (2/16) R filters transmitting the light of the wavelength band $H_R$. Hereinafter, in the case where a G filter is provided to the position corresponding to the pixel $P_{ij}$, the G filter is referred to as a $G_{ij}$. Similarly, in the case where a B filter is provided to the position corresponding to the pixel $P_{ij}$, the B filter is referred to as a $B_{ij}$, and in the case where an R filter is provided to the position corresponding to the pixel $P_{ij}$, the R filter is referred to as an $R_{ij}$.

Each of the read units C31 and C32 includes two filters where each transmits light of the same wavelength band. More specifically, in the read unit C31, the two G filters are arrayed in the row direction and each of the two G filters transmits the light of the wavelength band $H_G$. In the read unit C32, the two B filters are arrayed in the row direction and each of the two B filters transmits the light of the wavelength band $H_B$. Therefore, the basic unit C21 is configured with the two G filters which are adjacent to each other in the row direction and the two B filters which are adjacent to each other in the row direction.

In the read units C33 to C38, similarly, each read unit includes two filters where each transmits light of the same wavelength band. More specifically, in the read unit C33, the two R filters are arrayed in the row direction and each of the two R filters transmits the light of the wavelength band $H_R$. In the read unit C34, the two B filters are arrayed in the row direction and each of the two B filters transmits the light of the wavelength band $H_B$. Therefore, the basic unit C22 is configured with the two R filters which are adjacent to each other in the row direction and the two B filters which are adjacent to each other in the row direction.

In the read unit C35, the two G filters are arrayed in the row direction and each of the two G filters transmits the light of the wavelength band $H_G$. In the read unit C36, the two B filters are arrayed in the row direction and each of the two B filters transmits the light of the wavelength band $H_B$. Therefore, the basic unit C23 is configured with the two G filters which are adjacent to each other in the row direction and the two B filters which are adjacent to each other in the row direction.

In the read unit C37, the two G filters are arrayed in the row direction and each of the two G filters transmits the light of the wavelength band $H_G$. In the read unit C38, the two B filters are arrayed in the row direction and each of the two B filters transmits the light of the wavelength band $H_B$. Therefore, the basic unit C24 is configured with the two G filters which are adjacent to each other in the row direction and the two B filters which are adjacent to each other in the row direction.

In the filter unit C11, the read units C31, C33, C35, and C37 are disposed in the odd-numbered rows, and the read units C32, C34, C36, and C38 are disposed in the even-numbered rows. Each basic unit is configured with the read units which are adjacent to each other in the direction (column direction) perpendicular to the array direction (row direction) of the filters of the read units.

The reading unit 244f outputs the charges stored by each of the pixels of the light receiving unit 244e as the imaging signal by collectively reading the charges stored by the two pixels corresponding to each of the read units C31 to C38. For example, the reading unit 244f sums up the charges stored by each of the $G_{11}$ pixel and the $G_{12}$ pixel corresponding to the read unit C31 and converts the summed charges into a voltage (summed value) to generate the imaging signal.

When an F number of an objective optical system is denoted by Fno and a length of one side of a pixel of the light receiving unit 244e is denoted by Q (μm), the imaging optical system 243 satisfies 4.5 (/μm)≤Fno/Q 6.5 (/μm). The F number is an index indicating brightness of a lens and is a value obtained by dividing a focal length of the lens by an effective aperture.

Returning to FIGS. 1 and 2 for the description, the AFE unit 244b performs noise removal, A/D conversion, or the like on the imaging signal output by the sensor unit 244a. More specifically, the AFE unit 244b performs reduction of noise component included in the imaging signal (analog), adjustment of a signal amplification ratio (gain) for maintaining an output level, and A/D conversion of the analog imaging signal.

The P/S converter 244c (output unit) performs parallel/serial conversion on the digital imaging signal output by the AFE unit 244b. The P/S converter 244c outputs the imaging signal to the processing device 4 under the control of the imaging controller 244d.

The imaging controller 244d controls various operations of the distal end portion 24 according to setting data received from the processing device 4. The imaging controller 244d is configured with a central processing unit (CPU) and the like. The imaging controller 244d stores various programs for operating the endoscope 2, various parameters necessary for the operations of the endoscope 2, identification information of the endoscope 2, filter array information according to the color filter 244g, and the like.

The operating unit 22 includes a bending knob 221 bending the bending portion 25 in the up/down direction and the left/right direction, a treatment-tool insertion unit 222 inserting biological forceps, electric scalpel, and biopsy probes into a body cavity of a subject, and a plurality of switches 223 which are operation input units inputting operation instruction signals for peripheral devices such as an air supply means, a water supply means, and a screen display control in addition to the processing device 4 and the light source device 3. The treatment tool inserted from the treatment-tool insertion unit 222 is exposed to an opening (not illustrated) through a treatment-tool channel (not illustrated) of the distal end portion 24.

The universal cord 23 incorporates at least the above-described light guide 241 and a collective cable formed by bundling one signal line or a plurality of signal lines.

Next, a configuration of the light source device 3 will be described. The light source device 3 includes an illumination unit 31 and an illumination controller 32.

The illumination unit 31 switches to emit a plurality of illumination light beams, of which wavelength bands are different from each other under the control of the illumination controller 32. The illumination unit 31 includes a light source 33, a light source driver 34, a switching filter 35, a driving unit 36, and a driving-unit driver 37.

The light source 33 emits the white illumination light including the light of the red, green, and blue wavelength bands $H_B$, $H_G$, and $H_R$ under the control of the illumination controller 32. The white illumination light generated by the light source 33 is emitted from the distal end portion 24 through the switching filter 35 or the light guide 241 to the outside. The light source 33 is implemented by using a light source such as a white LED or a xenon lamp emitting the white light.

In addition, the light source 33 is not limited to a single lamp, but for example, a light source outputting a combination of light beams of different colors by using an LED emitting R color, an LED emitting G color, and an LED emitting B color may be used. In addition, a light source emitting desired light, for example, by a combination of a solid state light emitting element such as a laser diode emitting excitation light and a fluorescent substance emitting fluorescent light by the excitation light may be used.

The light source driver 34 supplies a current to the light source 33 to allow the light source 33 to emit the white illumination light under the control of the illumination controller 32.

The switching filter 35 transmits only the blue narrow-band light and the green narrow-band light among the white illumination light emitted by the light source 33. The switching filter 35 is insertably disposed on an optical path of the white illumination light emitted by the light source 33 under the control of the illumination controller 32. The switching filter 35 is disposed on the optical path of the white illumination light, so that the switching filter transmits only the light of the two narrow bands. More specifically, the switching filter 35 transmits the narrow-band illumination light including the light of the narrow-band $T_B$ (for example, 390 nm to 445 nm) included in the wavelength band $H_B$ and the light of the narrow-band $T_G$ (for example, 530 nm to 550 nm) included in the wavelength band $H_G$. The narrow-bands $T_B$ and $T_G$ are wavelength bands of blue light and green light which can be easily absorbed by hemoglobin in blood. In addition, the narrow-band $T_B$ may favorably include at least 405 nm to 425 nm. The light limited to the band to be emitted is referred to as narrow-band light (narrow-band illumination light), and image observation by using the narrow-band light is referred to as a narrow-band imaging (NBI) mode.

The driving unit 36 is configured with a step motor, a DC motor, or the like and operates the switching filter 35 to be inserted/withdrawn into/from the optical path of the light source 33.

The driving-unit driver 37 supplies a predetermined current to the driving unit 36 under the control of the illumination controller 32.

The illumination controller 32 controls the light source driver 34 to turn on or off the operation of the light source 33 and controls the driving-unit driver 37 to operate the switching filter 35 to be inserted/withdrawn into/from the optical path of the light source 33, so that the illumination controller controls a type (wavelength band) of the illumination light emitted by the illumination unit 31.

More specifically, the illumination controller 32 performs control of switching the illumination light emitted from the illumination unit 31 to any one of the white illumination light and the narrow-band illumination light by operating the switching filter 35 to be inserted/withdrawn into/from the optical path of the light source 33. In other words, the illumination controller 32 performs control of switching the imaging mode to any one of the white light imaging (WLI) mode using the white illumination light including the light of the wavelength bands $H_B$, $H_G$, and $H_R$ and the narrow-band imaging (NBI) mode using the narrow-band illumination light including the light of the narrow-bands $T_B$ and $T_G$.

Next, a configuration of the processing device 4 will be described. The processing device 4 includes an S/P converter 401, an image processing unit 402, an input unit 403, a recording unit 404, and a control unit 405.

The S/P converter 401 performs serial/parallel conversion on the serial imaging signal output from the distal end portion 24 and outputs the resulting signal to the image processing unit 402.

The image processing unit 402 generates an image signal (in-vivo image information) which is to be displayed by the display device 5 based on the imaging signal output from the S/P converter 401. The image processing unit 402 performs predetermined signal processes on the imaging signal to generate the image signal. As the signal processes, there are an optical black reduction process, a white balance adjustment process, a color matrix calculation process, a gamma correction process, a color reproduction process, an enhancement process including edge enhancement, and the like. In addition, the image processing unit 402 outputs the imaging signal input from the S/P converter 401 to the control unit 405.

The image processing unit 402 also includes a color component separation unit 402a and an extraction unit 402b. The color component separation unit 402a separates light components of the wavelength bands of the blue (B) wavelength band $H_B$, the green (G) wavelength band $H_G$, and the red (R) wavelength band $H_R$ from the electric signal output from the endoscope 2. More specifically, the color component separation unit 402a acquires pixel values of the pixels transmitting (receiving) the light of the designated colors and separates color component information including the pixel values of a single color component.

The extraction unit 402b applies a predetermined extraction process on the imaging signal. More specifically, the extraction unit 402b generates image information including extraction values for every color of red, green, and blue using respective the basic units C21 to C24 as one unit based on the imaging signals (summed values) from each of the pixels $P_{ij}$ corresponding to the read units C31 to C38.

The input unit 403 receives input of various signals such as an operation instruction signal of instructing operations of the endoscope system 1. The input unit 403 outputs the received signal to the control unit 405.

The recording unit 404 records data including various programs for operating the endoscope system 1, various parameters necessary for the operations of the endoscope system 1, and the like. The recording unit 404 is implemented by using a semiconductor memory such as a flash memory or a dynamic random access memory (DRAM).

The control unit 405 is configured with a CPU and the like and performs driving control of the endoscope 2 and configuration units including the light source device 3 and information input/output control with respect to the configuration units. The control unit 405 transmits setting data for imaging control through a predetermined signal line incorporated in the collective cable to the distal end portion 24. In addition, the control unit 405 reads exposing timing of the imaging process by the distal end portion 24 to output a synchronization signal including the timing to the distal end portion 24 and to output the synchronization signal to the light source device 3.

The display device 5 receives the in-vivo image corresponding to the in-vivo image information generated by the processing device 4 through a video cable and displays the in-vivo image. The display device 5 is configured with a liquid crystal display or an organic electro-luminescence (EL) display.

Figure 5:
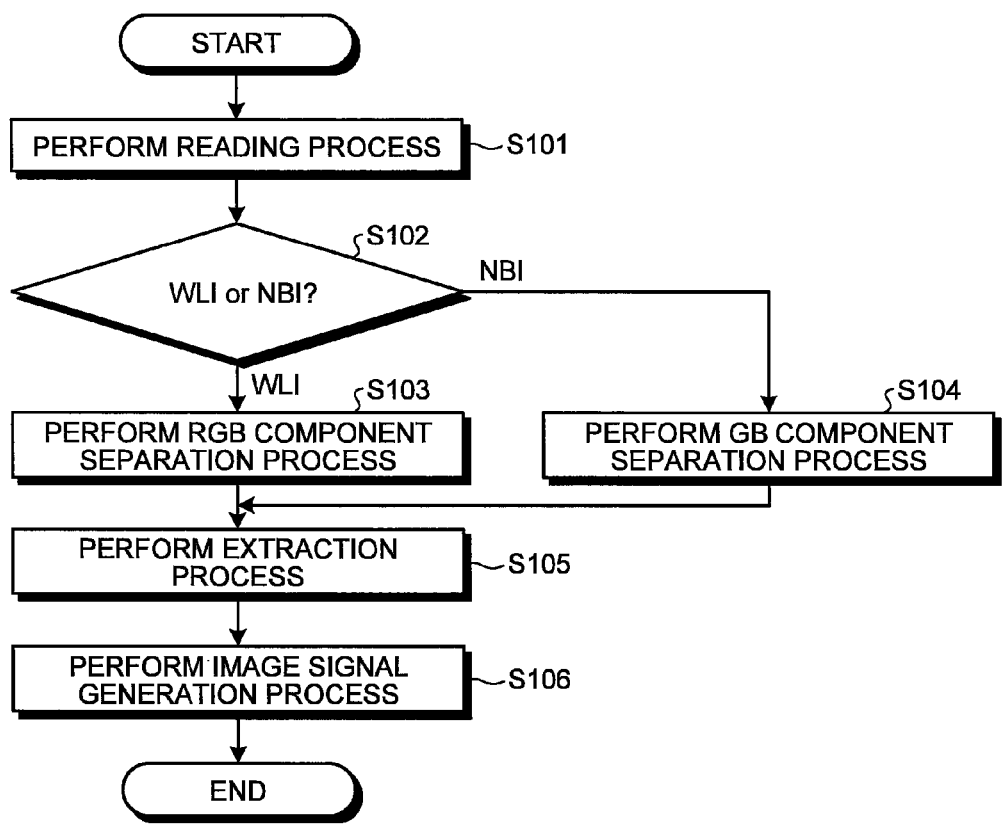
FIG. 5 is a flowchart illustrating a signal process performed by the endoscope system according to the first embodiment of the disclosure.

Next, the signal process performed by the endoscope system 1 will be described. FIG. 5 is a flowchart illustrating the signal process performed by the endoscope system according to the first embodiment. First, in the endoscope 2, under the control of the imaging controller 244d, a reading process by the reading unit 244f is performed (step S101). The reading unit 244f reads the charges stored by the plurality of pixels arrayed in a lattice shape for every row (line). Next, if the imaging signal from the endoscope 2 is received through the AFE unit 244b or the like, the control unit 405 determines whether the imaging mode is a white light imaging mode or a narrow-band imaging mode (step S102). The control unit 405 determines the imaging mode, for example, based on an insertion/withdrawal state of the switching filter 35, information of the illumination light assigned to the imaging signal, or the like.

In the case where it is determined by the control unit 405 that the imaging mode is the white light imaging mode (step S102: WLI), the color component separation unit 402a separates color component information of each color of the red, green, and blue components (RGB components) (step S103). On the other hand, in the case where it is determined by the control unit 405 that the imaging mode is the narrow-band imaging mode (step S102: NBI), the color component separation unit 402a separates color component information of each color of the green and blue components (GB components) (step S104).

FIG. 6 is a diagram explaining a color component acquisition mode of the sensor unit according to the first embodiment and is a diagram explaining acquisition of the red component from the R pixels. FIG. 7 is a diagram explaining a color component acquisition mode of the sensor unit according to the first embodiment and is a diagram explaining acquisition of the green component from the G pixels. FIG. 8 is a diagram explaining a color component acquisition mode of the sensor unit according to the first embodiment and is a diagram explaining acquisition of the blue component from the B pixels.

As illustrated in FIGS. 6 to 8, the light receiving unit 244e receives light according to the light of the wavelength bands transmitted by the filters of the color filter 244g. For this reason, the pixels of the light receiving unit 244e are different in terms of the wavelength bands of the received light according to the filters. For example, as illustrated in FIG. 6, the pixels receiving the light of the red component are R pixels (hatched pixels) such as an $R_{13}$ pixel, an $R_{14}$ pixel, an $R_{17}$ pixel, and an $R_{18}$ pixel. In addition, as illustrated in FIG. 7, the pixels receiving the light of the green component are G pixels (hatched pixels) such as a $G_{11}$ pixel, a $G_{12}$ pixel, a $G_{15}$ pixel, and a $G_{16}$ pixel. In addition, as illustrated in FIG. 8, the pixels receiving the light of the blue component are B pixels (hatched pixels) such as a $B_{21}$ pixel, a $B_{22}$ pixel, a $B_{23}$ pixel, and a $B_{24}$ pixel.

The color component separation unit 402a separates pixel values (summed values) of each of the R, G, and B pixels for every color according to to-be-separated color components and outputs the separated pixel values as color component information in association with the position (pixel $P_{ij}$) of the pixels.

If the color components are separated according to the imaging mode by the color component separation unit 402a, the extraction unit 402b performs an extraction process (step S105). FIG. 9 is a diagram explaining the extraction process in the extraction unit according to the first embodiment and is a diagram explaining an extraction area. The extraction unit 402b generates image information having the extraction values using respective the basic units C21 to C24 as a unit based on the imaging signals form the pixels $P_{ij}$ corresponding to the read units C31 to C38. More specifically, as illustrated in FIG. 9, the extraction unit extracts the summed value according to the color components for an area configured with four pixels (area corresponding to each of the basic units C21 to C24) as one color component area (extraction area). In FIG. 9, the extraction area disposed at the m-th row and n-column is denoted by $S_{mn}$. For example, the extraction area $S_{11}$ corresponds to the basic unit C21, the extraction area $S_{12}$ corresponds to the basic unit C22, the extraction area $S_{21}$ corresponds to the basic unit C23, and the extraction area $S_{22}$ corresponds to the basic unit C24.

The extraction unit 402b generates extraction image information where the extraction values for every extraction area are set based on the color component information of each color extracted by the color component separation unit 402a. In the case where the imaging mode is the white light imaging mode, the extraction unit 402b generates extraction image information of each of the red, green, and blue components; and in the case where the imaging mode is the narrow-band imaging mode, the extraction unit generates extraction image information of each of the green and blue components. For example, in the case where the extraction unit generates the extraction image information of the red component, the extraction unit 402b acquires the color component information of the red component separated by the color component separation unit 402a. Herein, the color component information separated by the color component separation unit 402a is information according to the pixel values and the array of the R pixels (refer to FIG. 6). In the case where the read units configured with the R pixels are included in the extraction area $S_{mn}$, the extraction unit 402b defines the summed values obtained by the read units as the extraction values of the extraction area. More specifically, for example, since the extraction area $S_{12}$ includes the read unit C33 configured with the $R_{13}$ pixel and the $R_{14}$ pixel, the extraction unit 402b sets the summed values obtained by the read unit C33 as the extraction value of the extraction area $S_{12}$.

Figure 10:
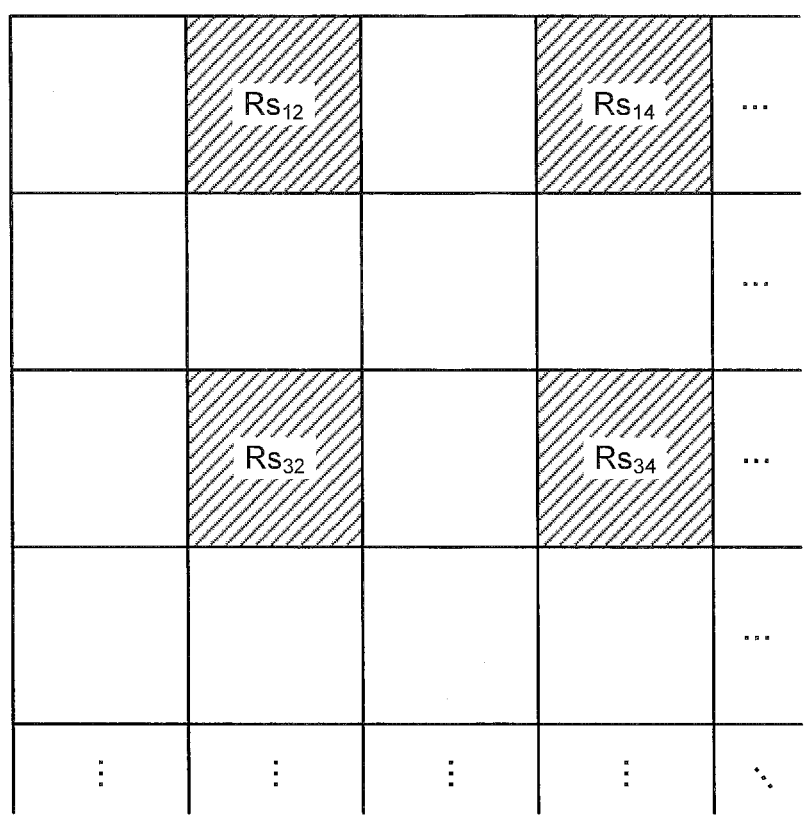
FIG. 10 is a diagram explaining an extraction process of the extraction unit according to the first embodiment of the disclosure and is a diagram illustrating an extraction image with respect to a red component.

FIG. 10 is a diagram explaining the extraction process in the extraction unit according to the first embodiment and is a diagram illustrating an extraction image with respect to the red component. As described above, if the extraction unit performs the extraction process on the extraction area $S_{mn}$ where the read units having the R pixels exist, the extraction unit 402b generates the extraction image information including the extraction image where the extraction values of the red component are set (refer to FIG. 10). In FIG. 10, the extraction area $S_{mn}$ disposed at the m-th row and n-column is denoted by $Rs_{mn}$ according to the color components (red in FIG. 10).

Figure 11:
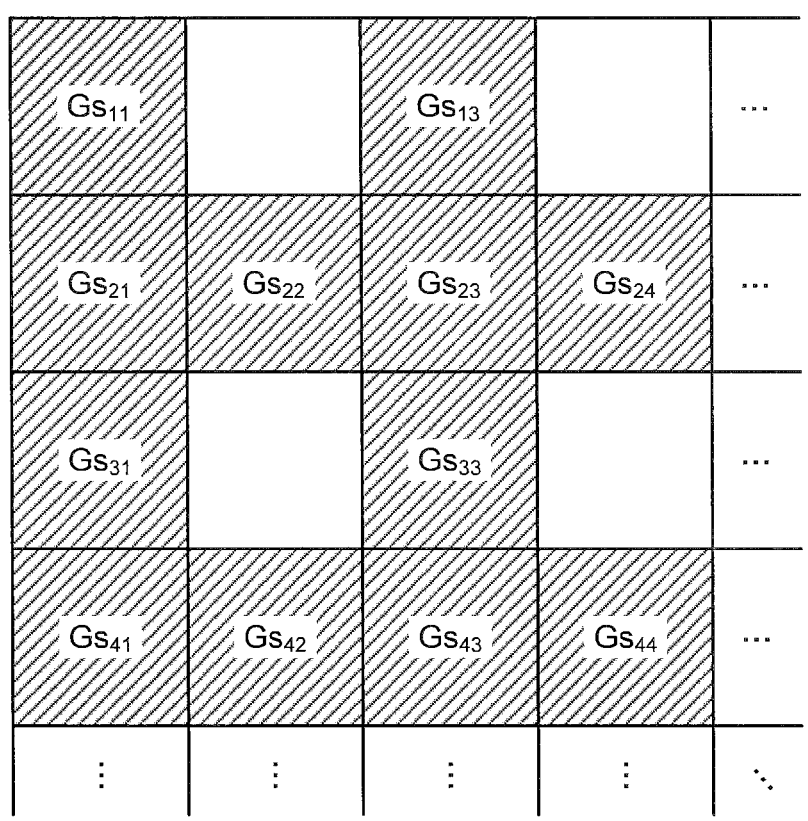
FIG. 11 is a diagram explaining an extraction process of the extraction unit according to the first embodiment of the disclosure and is a diagram illustrating an extraction image with respect to a green component.

FIG. 11 is a diagram explaining the extraction process in the extraction unit according to the first embodiment and is a diagram illustrating an extraction image with respect to the green component. FIG. 12 is a diagram explaining the extraction process in the extraction unit according to the first embodiment and is a diagram illustrating an extraction image with respect to the blue component. Similarly to the red component, the extraction unit 402b performs the extraction process on the green and blue components to generate the extraction image information. In addition, with respect to the blue component, since all the basic units include the read unit configured with the B pixels, all the extraction areas $S_{mn}$ are replaced with the summed values of the B pixels (refer to FIG. 12). In FIGS. 11 and 12, the extraction area disposed at the m-th row and the n-th column is denoted by $Gs_{mn}$ or $Bs_{mn}$ according to the green component or the blue component.

If the extraction image information on each of the color components is generated by the extraction unit 402b, the image processing unit 402 generates the image signal which is to be displayed on the display device 5 based on the extraction image information (step S106). The image processing unit 402 performs an interpolation process on the extraction values of each of the color components for every extraction area $S_{mn}$ based on the extraction image information of each of the color components according to the imaging mode to generate a monochromatic image where the extraction values or the extraction values (interpolation values) obtained by interpolation of the interpolation process are assigned to all the extraction areas. In the white light imaging mode, the image processing unit 402 performs the interpolation process by using the green component as a luminance component; and in the narrow-band imaging mode, the image processing unit performs the interpolation process by using the blue component as a luminance component.

Subsequently, the image processing unit 402 generates a color image signal according to the color image by using the extraction values or the interpolation values of each of the monochromatic images. By the above-described signal process, each image can be obtained based on the signals acquired by the white light imaging mode and the narrow-band imaging mode.

In the above-described signal process, since in the white light imaging mode, the color component information of each of the red, green, and blue components can be obtained; in the narrow-band imaging mode, the color component information of each of the green and blue components can be obtained; and a lot of the color component information of the blue component can be obtained, particularly, it is possible to clarify the image by the narrow-band imaging mode.

According to the above-described first embodiment, the filter unit C11 is configured with the six G filters transmitting the light of the wavelength band $H_G$, the eight B filters transmitting the light of the wavelength band $H_B$, and the two R filters transmitting the light of the wavelength band $H_R$, the extraction unit 402b is configured to generate the extraction image information of the extraction area configured with the four pixels corresponding to each of the basic units C21 to C24 based on the color component information extracted by the color component separation unit 402a, and the image processing unit 402 is configured to generate the color image signal. Therefore, it is possible to obtain a clear image in any one of the white light imaging mode and the narrow-band imaging mode.

In addition, according to the above-described first embodiment, since the summed charges obtained from the two pixels constituting the read unit are read, in comparison with the case where the imaging signal based on the charges obtained from all the pixels is transmitted, the information amount transmitted from the endoscope 2 to the processing device 4 can be reduced. For example, in the case where the light receiving unit 244e is configured with 8×8 (=64) pixels, the information amount for the 32 pixels is favorably transmitted. Therefore, the diameter of the cable connecting the endoscope 2 and the processing device 4 can be reduced, so that a small size of the endoscope system 1 can be implemented. In addition, since the pixels as the summation objects receive the light of the same wavelength band, there is no mixture of information between the color components.

Modified Example of First Embodiment

FIG. 13 is a schematic diagram illustrating an example of a configuration of a color filter according to a modified example of the first embodiment of the disclosure. A filter unit C11a according to the modified example is partitioned into basic units C21a to C24a which are four areas divided in 2 rows×2 columns. In addition, the basic units C21a to C24a are partitioned into read units C31a to C38a formed by dividing each basic unit in 1 row×2 columns. More specifically, the basic unit C21a is divided in 1 row×2 columns to include the read units C31a and C32a, the basic unit C22a is divided in 1 row×2 columns to include the read units C33a and C34a, the basic unit C23a is divided in 1 row×2 columns to include the read units C35a and C36a, and the basic unit C24a is divided in 1 row×2 columns to include the read units C37a and C38a, As illustrated in FIG. 13, the filter unit C11a according to the modified example is configured with the eight (8/16) G filters transmitting the light of the wavelength band $H_G$, the six (6/16) B filters transmitting the light of the wavelength band $H_B$, and the two (2/16) R filters transmitting the light of the wavelength band $H_R$.

Each of the read units C31a and C32a includes two filters where each transmits light of the same wavelength band. More specifically, in the read unit C31a, the two B filters are arrayed in the row direction and each of the two B filters transmits the light of the wavelength band $H_B$. In the read unit C32a, the two G filters are arrayed in the row direction and each of the two G filters transmits the light of the wavelength band $H_G$. Therefore, the basic unit C21a is configured with the two B filters which are adjacent to each other in the row direction and the two G filters which are adjacent to each other in the row direction.

In the read units C33a to C38a, similarly, each read unit includes two filters where each transmits light of the same wavelength band. More specifically, in the read unit C33a, the two R filters are arrayed in the row direction and each of the two R filters transmits the light of the wavelength band $H_R$. In the read unit C34a, the two G filters are arrayed in the row direction and each of the two G filters transmits the light of the wavelength band $H_G$. Therefore, the basic unit C22a is configured with the two R filters which are adjacent to each other in the row direction and the two G filters which are adjacent to each other in the row direction.

In the read unit C35a, the two B filters are arrayed in the row direction and each of the two B filters transmits the light of the wavelength band $H_B$. In the read unit C36a, the two G filters are arrayed in the row direction and each of the two G filters transmits the light of the wavelength band $H_G$. Therefore, the basic unit C23a is configured with the two G filters which are adjacent to each other in the row direction and the two B filters which are adjacent to each other in the row direction.

In the read unit C37a, the two B filters are arrayed in the row direction and each of the two B filters transmits the light of the wavelength band $H_B$. In the read unit C38a, the two G filters are arrayed in the row direction and each of the two G filters transmits the light of the wavelength band $H_G$. Therefore, the basic unit C24a is configured with the two G filters which are adjacent to each other in the row direction and the two B filters which are adjacent to each other in the row direction.

In the filter unit C11a, the read units C31a, C33a, C35a, and C37a are disposed in the odd-numbered rows, and the read units C32a, C34a, C36a, and C38a are disposed in the even-numbered rows.

In the filter unit according to the embodiment, similarly to the above-described first embodiment, it is possible to obtain the effect in that a clear image can be obtained in any one of the white light imaging mode and the narrow-band imaging mode.

Second Embodiment

Figure 14:
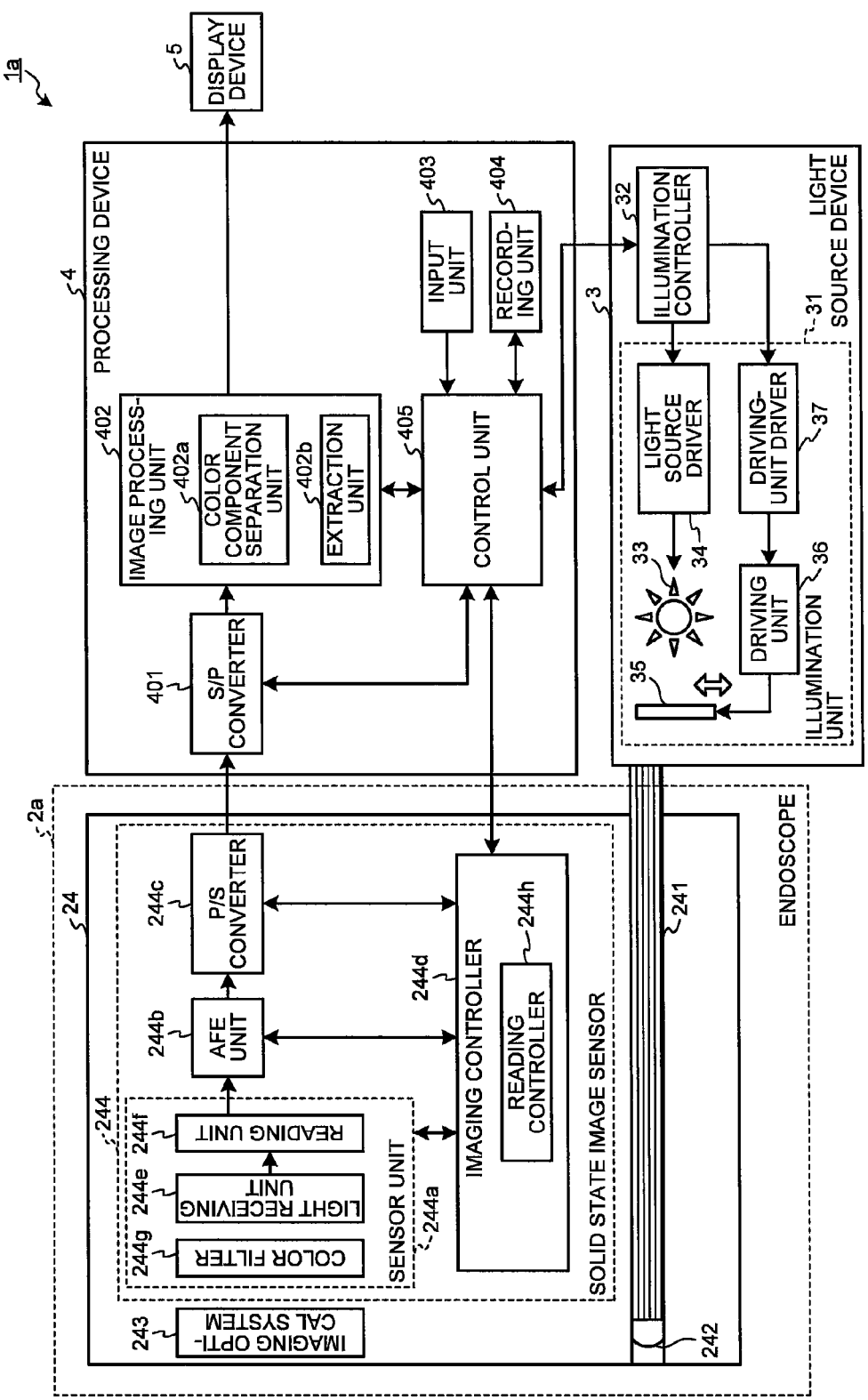
FIG. 14 is a block diagram illustrating a schematic configuration of an endoscope system according to a second embodiment of the disclosure.

Next, a second embodiment of the disclosure will be described. FIG. 14 is a block diagram illustrating a schematic configuration of an endoscope system according to the second embodiment of the disclosure. The same components as those of the above-described components are denoted by the same reference signs. An endoscope system 1a according to the second embodiment includes an endoscope 2a instead of the endoscope 2 according to the above-described first embodiment, and the endoscope 2a further includes a reading controller 244h besides the configuration of the above-described endoscope 2.

The reading controller 244h selects the row of the to-be-read pixels according to the imaging mode and allows a reading unit 244f to perform reading of the pixels (read units) of the selected row. The reading unit 244f performs reading of charges stored by the pixels (read units) of the designated row (more specifically, odd-numbered row or even-numbered row) under the control of the reading controller 244h.

FIG. 15 is a schematic diagram illustrating an example of a configuration of a color filter according to the second embodiment. In the second embodiment, for example, a color filter 244g is configured so that filter units C11b configured with sixteen filters aligned in a 4×4 matrix shape are disposed to be aligned two-dimensionally (in a matrix shape) according to the array of pixels $P_{ij}$.

The filter unit C11b is partitioned into basic units C21b to C24b which are four areas divided in 2 rows×2 columns. In addition, the basic units C21b to C24b are partitioned into read units C31b to C38b which are formed by dividing each basic unit in 1 row×2 columns. More specifically, the basic unit C21b is divided in 1 row×2 columns to include read units C31b and C32b, the basic unit C22b is divided in 1 row×2 columns to include read units C33b and C34b, the basic unit C23b is divided in 1 row×2 columns to include read units C35b and C36b, and the basic unit C24b is divided in 1 row×2 columns to include read units C37b and C38b.

As illustrated in FIG. 15, the filter unit C11b according to the second embodiment is configured with eight (8/16) G filters transmitting the light of the wavelength band $H_G$, the six (6/16) B filters transmitting the light of the wavelength band $H_G$, and the two (2/16) R filters transmitting the light of the wavelength band $H_R$.

Each of the read units C31b and C32b includes two filters where each transmits light of the same wavelength band. More specifically, in the read unit C31b, the two G filters are arrayed in the row direction and each of the two G filters transmits the light of the wavelength band $H_G$. In the read unit C32b, the two B filters are arrayed in the row direction and each of the two B filters transmits the light of the wavelength band $H_B$. Therefore, the basic unit C21b is configured with the two G filters which are adjacent to each other in the row direction and the two B filters which are adjacent to each other in the row direction.

In the read units C33b to C38b, similarly, each read unit includes two filters where each transmits light of the same wavelength band. More specifically, in the read unit C33b, the two R filters are arrayed in the row direction and each of the two R filters transmits the light of the wavelength band $H_R$. In the read unit C34b, the two G filters are arrayed in the row direction and each of the two G filters transmits the light of the wavelength band $H_G$. Therefore, the basic unit C22b is configured with the two R filters which are adjacent to each other in the row direction and the two G filters which are adjacent to each other in the row direction.

In the read unit C35b, the two B filters are arrayed in the row direction and each of the two B filters transmits the light of the wavelength band $H_B$. In the read unit C36b, the two G filters are arrayed in the row direction and each of the two G filters transmits the light of the wavelength band $H_G$. Therefore, the basic unit C23b is configured with the two G filters which are adjacent to each other in the row direction and the two B filters which are adjacent to each other in the row direction.

In the read unit C37b, the two G filters are arrayed in the row direction and each of the two G filters transmits the light of the wavelength band $H_G$. In the read unit C38b, the two B filters are arrayed in the row direction and each of the two B filters transmits the light of the wavelength band $H_B$. Therefore, the basic unit C24b is configured with the two G filters which are adjacent to each other in the row direction and the two B filters which are adjacent to each other in the row direction.

In the filter unit C11b, the read units C31b, C33b, C35b, and C37b are disposed in the odd-numbered rows, and the read units C32b, C34b, C36b, and C38b are disposed in the even-numbered rows.

The reading unit 244f outputs the charges stored by the plurality of pixels of the light receiving unit 244e as the imaging signal by collectively reading in each of the read units C31b to C38b. For example, the reading unit 244f sums up the charges stored by each of the $G_{11}$ pixel and the $G_{12}$ pixel corresponding to the read unit C31b and converts the summed charges into a voltage (summed value) to generate the imaging signal. The reading unit 244f reads the charges of the pixels of the read units disposed in any one row of the odd-numbered rows or the even-numbered rows under the control of the reading controller 244h.

Figure 16:
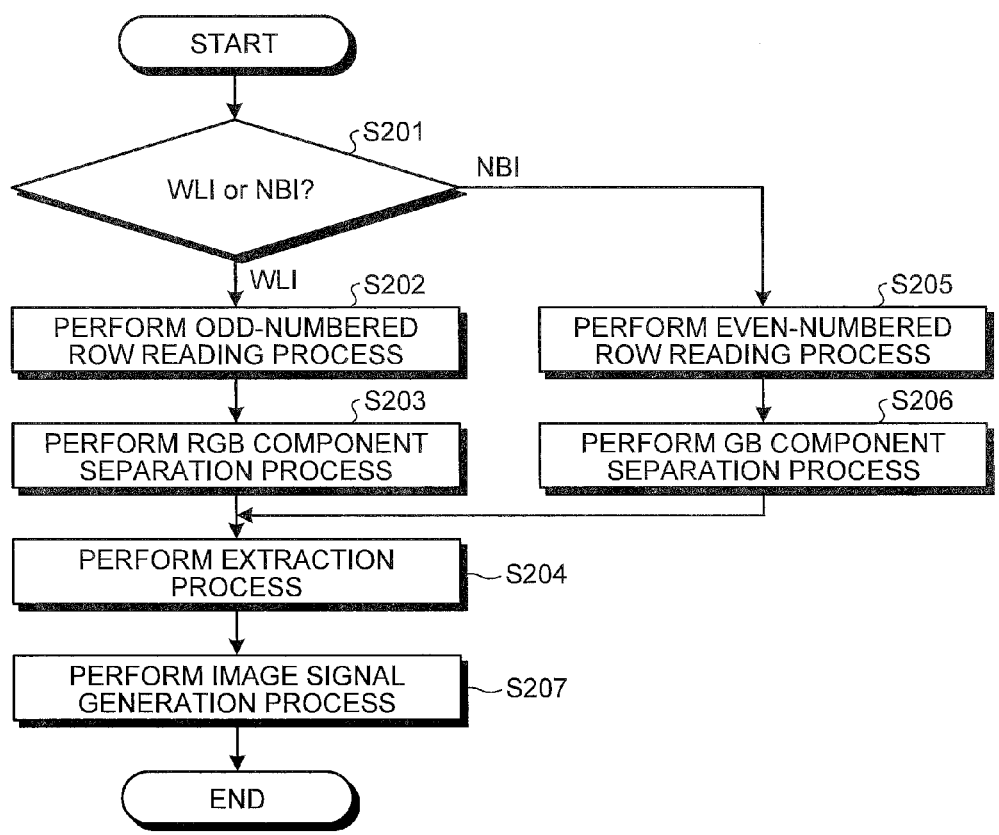
FIG. 16 is a flowchart illustrating a signal process performed by the endoscope system according to the second embodiment of the disclosure.

FIG. 16 is a flowchart illustrating a signal process performed by the endoscope system according to the second embodiment. First, the control unit 405 determines whether an imaging mode is a white light imaging mode or a narrow-band imaging mode and outputs a determination result to an imaging controller 244d (reading controller 244h) (step S201). In the case where the received determination result is the white light imaging mode (step S201: WLI), the reading controller 244h allows the reading unit 244f to perform a reading process on the pixels of the odd-numbered rows (step S202). FIG. 17 is a diagram explaining a charge reading mode of a sensor unit according to the second embodiment and is a diagram explaining reading of the pixels of the odd-numbered rows. The reading unit 244f performs the charge reading process on the pixels (hatched pixels in FIG. 17) of the odd-numbered rows.

If the charge reading process on the pixels of the odd-numbered rows by the reading unit 244f is ended, a generated imaging signal is output through the AFE unit 244b and the like from the endoscope 2a to the processing device 4. If the processing device 4 receives the imaging signal through the AFE unit 244b and the like from the endoscope 2a, the color component separation unit 402a separates color component information of each of colors of red, green, and blue components (RGB components) (step S203).

Figure 18:
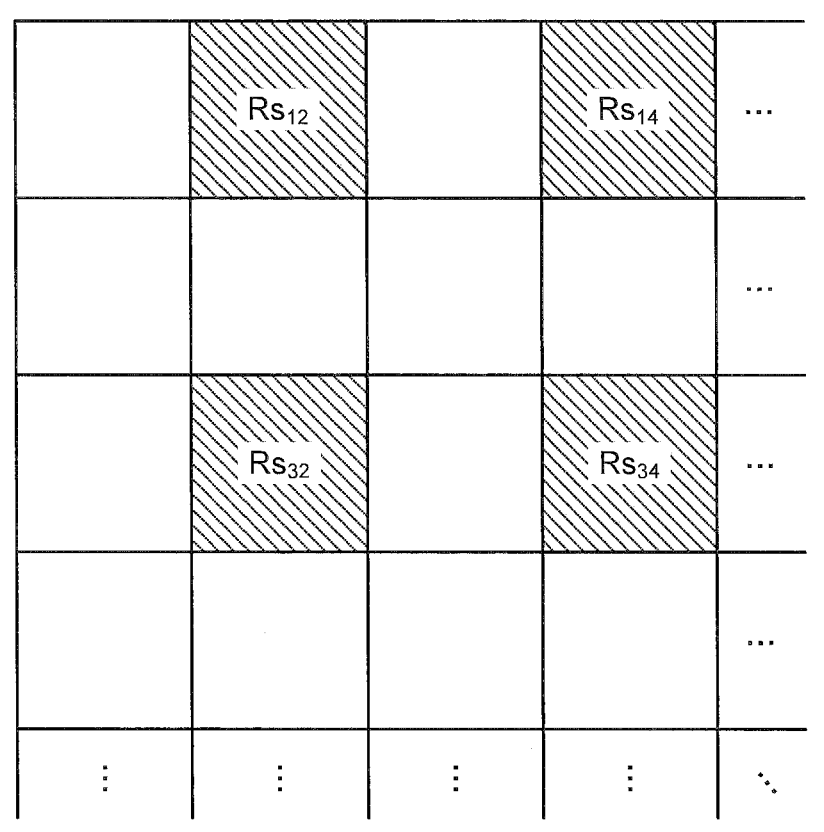
Figure 19:
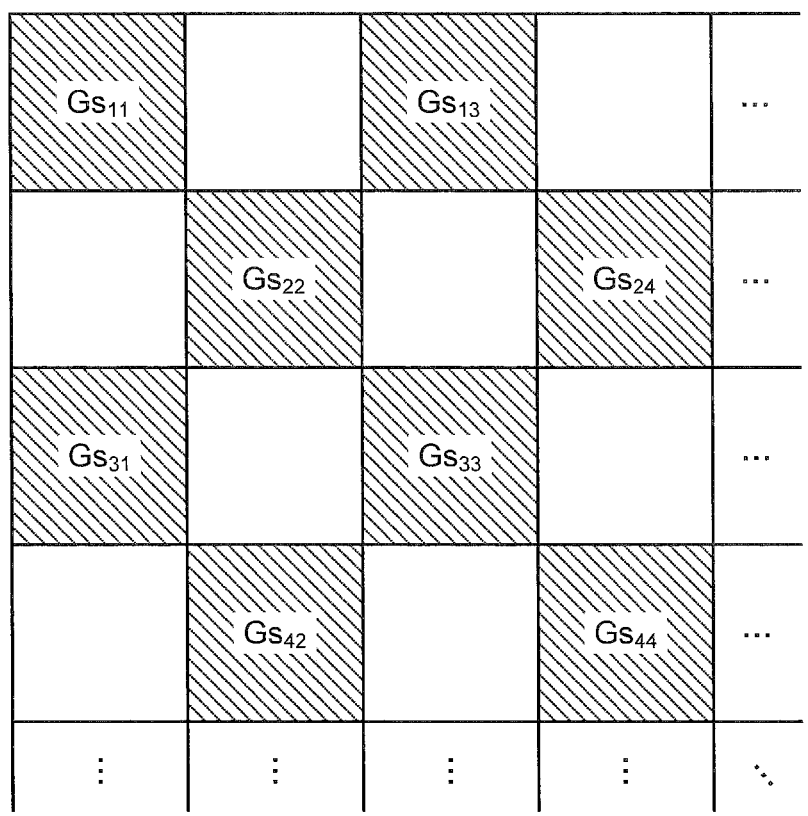
FIG. 19 is a diagram explaining an extraction process of the extraction unit according to the second embodiment of the disclosure and is a diagram illustrating an extraction image with respect to a green component.
Figure 20:
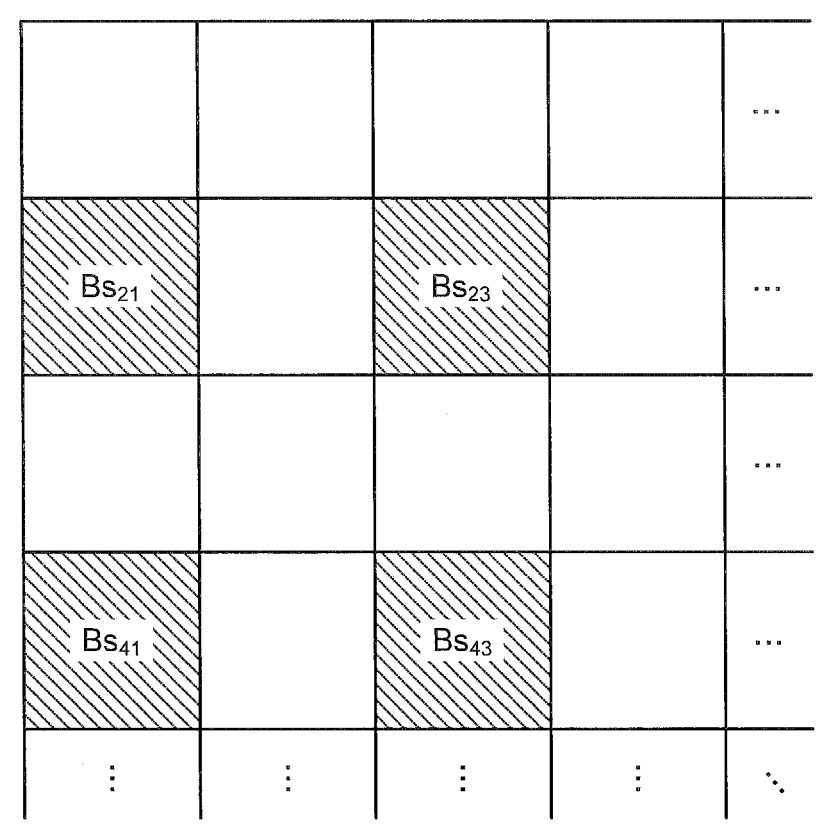

FIG. 18 is a diagram explaining a signal conversion process of the extraction unit according to the second embodiment and is a diagram illustrating an extraction image with respect to the red component. FIG. 19 is a diagram explaining an extraction process of the extraction unit according to the second embodiment and is a diagram illustrating an extraction image with respect to the green component. FIG. 20 is a diagram explaining an extraction process of the extraction unit according to the second embodiment and is a diagram illustrating an extraction image with respect to the blue component.

If the color components (RGB components) are extracted by the color component separation unit 402a, the extraction unit 402b performs an extraction process (step S204). Similarly to step S105 described above, the extraction unit 402b performs the extraction process on the extraction area $S_{mn}$ for every color component. Extraction image information for every color component as illustrated in FIGS. 18 to 20 is generated by the extraction process of the extraction unit 402b.

On the other hand, in the case where the received determination result is the narrow-band imaging mode (step S201: NBI), the reading controller 244h allows the reading unit 244f to perform a reading process on the pixels of the even-numbered rows (step S205). FIG. 21 is a diagram explaining a charge reading mode of a sensor unit according to the second embodiment and is a diagram explaining reading of the pixels of the even-numbered rows. The reading unit 244f performs the charge reading process on the pixels (hatched pixels in FIG. 21) of the even-numbered rows.

If the charge reading process on the pixels of the even-numbered rows by the reading unit 244f is ended, a generated imaging signal is output through the AFE unit 244b and the like from the endoscope 2a to the processing device 4. If the processing device 4 receives the imaging signal through the AFE unit 244b and the like from the endoscope 2a, the color component separation unit 402a separates color component information of each of colors of the green and blue components (GB components) (step S206).

Figure 22:
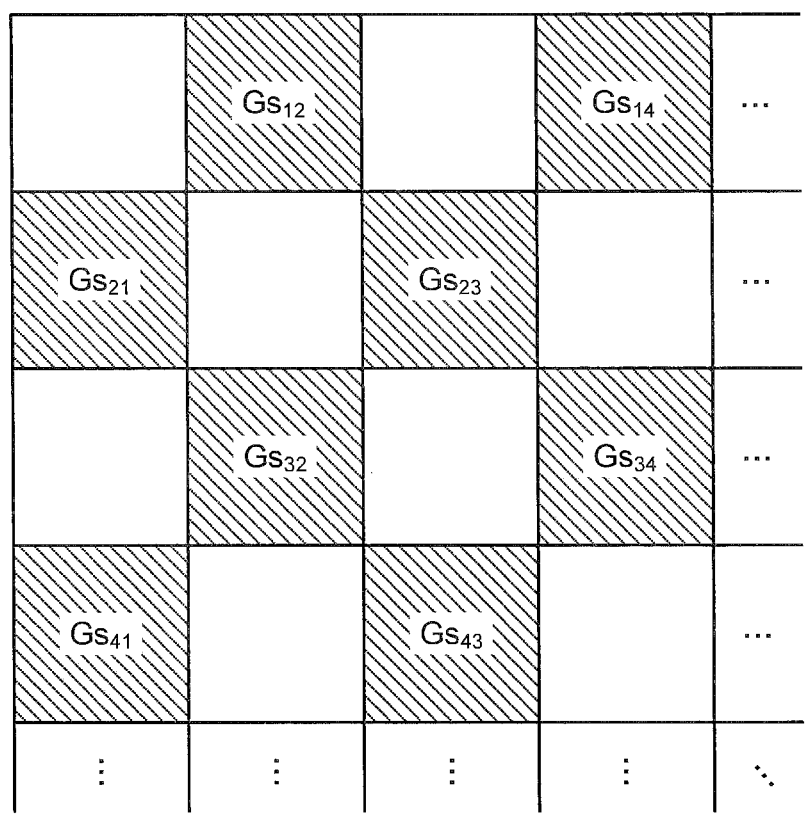
FIG. 22 is a diagram explaining an extraction process of the extraction unit according to the second embodiment of the disclosure and is a diagram illustrating an extraction image with respect to the green component.
Figure 23:
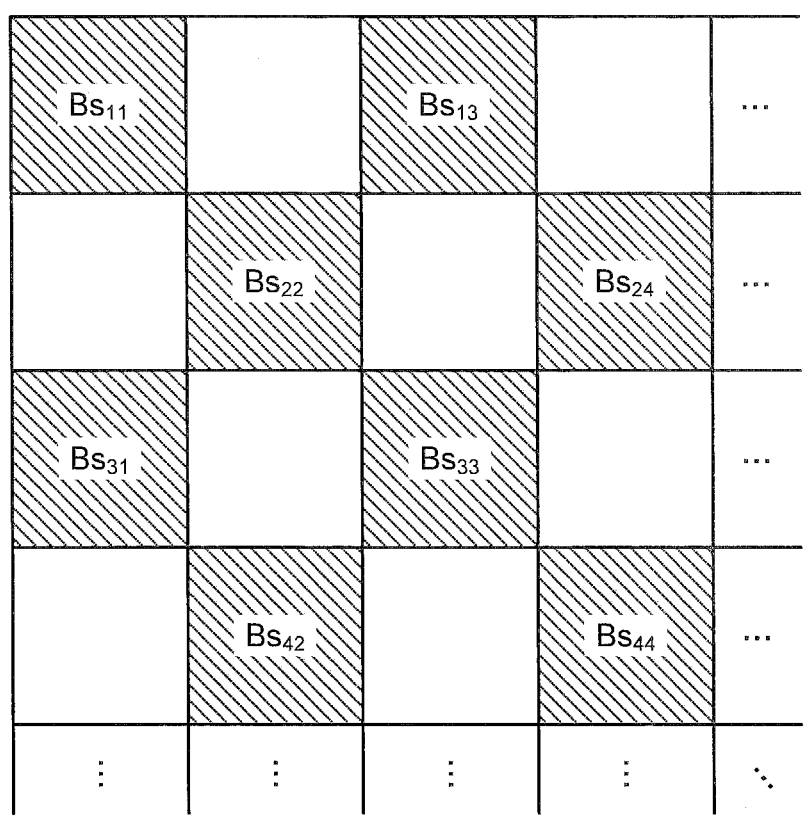
FIG. 23 is a diagram explaining an extraction process of the extraction unit according to the second embodiment of the disclosure and is a diagram illustrating an extraction image with respect to the blue component.

FIG. 22 is a diagram explaining an extraction process of the extraction unit according to the second embodiment and is a diagram illustrating an extraction image with respect to the green component. FIG. 23 is a diagram explaining an extraction process of the extraction unit according to the second embodiment and is a diagram illustrating an extraction image with respect to the blue component.

If color components (GB components) are extracted by the color component separation unit 402a in step S206, the extraction unit 402b performs an extraction process (step S204). The extraction unit 402b performs the extraction process on the extraction area $S_{mn}$ for every color component. Extraction image information for every color component as illustrated in FIGS. 22 and 23 is generated by the extraction process of the extraction unit 402b.

If the extraction image information for each color component is generated by the extraction unit 402b, the image processing unit 402 generates an image signal which is to be displayed on a display device 5 based on the extraction image information (step S207). The image processing unit 402 performs an interpolation process on the extraction values of each color component for every extraction area based on the extraction image signal of each of the color components according to the imaging mode to generate a monochromatic image where extraction values or interpolation value are assigned to all the extraction areas. In the white light imaging mode, the image processing unit 402 performs the interpolation process by using the green component as a luminance component; and in the narrow-band imaging mode, the image processing unit performs the interpolation process by using the blue component as a luminance component.

Subsequently, the image processing unit 402 generates a color image signal according to the color image by using the extraction values or the interpolation values of each of the monochromatic images. By the above-described signal process, each image can be obtained based on the signals acquired by the white light imaging mode and the narrow-band imaging mode.

In the above-described signal process, since in the white light imaging mode, the color component information of each of the red, green, and blue components can be obtained; in the narrow-band imaging mode, the color component information of each of the green and blue components can be obtained; and a lot of the color component information of the blue component can be obtained, particularly, it is possible to clarify the image by the narrow-band imaging mode.

According to the above-described second embodiment, similarly to the first embodiment, the filter unit C11b is configured with the eight G filters transmitting the light of the wavelength band $H_G$, the six B filters transmitting the light of the wavelength band $H_B$, and the two R filters transmitting the light of the wavelength band $H_R$, the extraction unit 402b is configured to generate the extraction image information of the extraction area configured with four pixels corresponding to each of the basic units C21b to C24b based on the color component information extracted by the color component separation unit 402a, and the image processing unit 402 is configured to generate the color image signal. Therefore, it is possible to obtain a clear image in any one of the white light imaging mode and the narrow-band imaging mode.

In addition, according to the above-described second embodiment, since the summed charges obtained from the two pixels constituting the read unit are read, in comparison with the case where the electric signal based on the charges obtained from all the pixels is transmitted, the information amount transmitted from the endoscope 2a to the processing device 4 can be reduced. For example, in the case where the light receiving unit 244e is configured with 8×8 (=64) pixels, the information amount for the 32 pixels is favorably transmitted. Therefore, the diameter of the cable connecting the endoscope 2a and the processing device 4 can be reduced, so that a small size of the endoscope system 1a can be implemented. In addition, since the pixels as the summation objects receive the light of the same wavelength band, there is no mixture of information between the color components.

In addition, according to the above-described second embodiment, since the row of the to-be-read pixels is controlled according to the imaging mode, in comparison with the case where the electric signal based on the charges obtained from the entire pixels is transmitted or the above-described first embodiment, it is possible to reduce an information amount transmitted from the endoscope 2a to the processing device 4. Therefore, the diameter of the cable connecting the endoscope 2a and the processing device 4 can be reduced, so that a small size of the endoscope system 1a can be implemented.

In addition, in the above-described second embodiment, the reading unit 244f may perform reading on the entire pixels, and the color component separation unit 402a may separate the luminance values (signal) of the odd-numbered rows or the even-numbered rows according to the imaging mode. Therefore, it is possible to reduce load of an image signal generation process by the image processing unit 402.

Modified Example 1 of Second Embodiment

FIG. 24 is a schematic diagram illustrating an example of a configuration of a color filter according to Modified Example 1 of the second embodiment of the disclosure. A filter unit C11c according to the modified example is partitioned into basic units C21c to C24c which are four areas divided in 2 rows×2 columns. In addition, the basic units C21c to C24c are partitioned into read units C31c to C38c which are formed by dividing each basic unit in 1 row×2 columns. More specifically, the basic unit C21c is divided in 1 row×2 columns to include read units C31c and C32c, the basic unit C22c is divided in 1 row×2 columns to include read units C33c and C34c, the basic unit C23c is divided in 1 row×2 columns to include read units C35c and C36c, and the basic unit C24c is divided in 1 row×2 columns to include read units C37c and C38c.

As illustrated in FIG. 24, a filter unit C11c according to Modified Example 1 is configured with six (6/16) G filters transmitting the light of the wavelength band $H_G$, eight (8/16) B filters transmitting the light of the wavelength band $H_B$, and two (2/16) R filters transmitting the light of the wavelength band $H_R$.

Each of the read units C31c and C32c includes two filters where each transmits light of the same wavelength band. More specifically, in the read unit C31c, the two B filters are arrayed in the row direction and each of the two B filters transmits the light of the wavelength band $H_B$. In the read unit C32c, the two G filters are arrayed in the row direction and each of the two G filters transmits the light of the wavelength band $H_G$. Therefore, the basic unit C21c is configured with the two B filters which are adjacent to each other in the row direction and the two G filters which are adjacent to each other in the row direction.

In the read units C33c to C38c, similarly, each read unit includes two filters where each transmits light of the same wavelength band. More specifically, in the read unit C33c, the two R filters are arrayed in the row direction and each of the two R filters transmits the light of the wavelength band $H_R$. In the read unit C34c, the two B filters are arrayed in the row direction and each of the two B filters transmits the light of the wavelength band $H_B$. Therefore, the basic unit C22c is configured with the two R filters which are adjacent to each other in the row direction and the two B filters which are adjacent to each other in the row direction.

In the read unit C35c, the two B filters are arrayed in the row direction and each of the two B filters transmits the light of the wavelength band $H_B$. In the read unit C36c, the two G filters are arrayed in the row direction and each of the two G filters transmits the light of the wavelength band $H_G$. Therefore, the basic unit C23c is configured with the two G filters which are adjacent to each other in the row direction and the two B filters which are adjacent to each other in the row direction.

In the read unit C37c, the two G filters transmitting the light of the wavelength band $H_G$ are arrayed in the row direction and each of the two G filters transmits the light of the wavelength band $H_G$. In the read unit C38c, the two B filters are arrayed in the row direction and each of the two B filters transmits the light of the wavelength band $H_B$. Therefore, the basic unit C24c is configured with the two B filters which are adjacent to each other in the row direction and the two G filters which are adjacent to each other in the row direction.

In the filter unit C11c, the read units C31c, C33c, C35c, and C37c are disposed in the odd-numbered rows, and the read units C32c, C34c, C36c, and C38c are disposed in the even-numbered rows.

Modified Example 2 of Second Embodiment

FIG. 25 is a schematic diagram illustrating an example of a configuration of a color filter according to Modified Example 2 of the second embodiment of the disclosure. A filter unit C11d according to the modified example is partitioned into basic units C21d to C24d which are four areas divided in 2 rows×2 columns. In addition, the basic units C21d to C24d are partitioned into read units C31d to C38d which are formed by dividing each basic unit in 1 row×2 columns. More specifically, the basic unit C21d is divided in 1 row×2 columns to include read units C31d and C32d, the basic unit C22d is divided in 1 row×2 columns to include read units C33d and C34d, the basic unit C23d is divided in 1 row×2 columns to include read units C35d and C36d, and the basic unit C24d is divided in 1 row×2 columns to include read units C37d and 038d.

As illustrated in FIG. 25, the filter unit C11d according to Modified Example 2 is configured with eight (8/16) G filters transmitting the light of the wavelength band $H_G$, six (6/16) B filters transmitting the light of the wavelength band $H_B$, and two (2/16) R filters transmitting the light of the wavelength band $H_R$.

Each of the read units C31d and C32d includes two filters where each transmits light of the same wavelength band. More specifically, in the read unit C31d, the two G filters are arrayed in the row direction and each of the two G filters transmits the light of the wavelength band $H_G$. In the read unit C32d, the two B filters are arrayed in the row direction and each of the two B filters transmits the light of the wavelength band $H_B$. Therefore, the basic unit C21d is configured with the two G filters which are adjacent to each other in the row direction and the two B filters which are adjacent to each other in the row direction.

In the read units C33d to C38d, similarly, each read unit includes two filters where each transmits light of the same wavelength band. More specifically, in the read unit C33d, the two R filters are arrayed in the row direction and each of the two R filters transmits the light of the wavelength band $H_R$. In the read unit C34d, the two G filters are arrayed in the row direction and each of the two G filters transmits the light of the wavelength band $H_G$. Therefore, the basic unit C22d is configured with the two R filters which are adjacent to each other in the row direction and the two G filters which are adjacent to each other in the row direction.

In the read unit C35d, the two G filters are arrayed in the row direction and each of the two G filters transmits the light of the wavelength band $H_G$. In the read unit C36d, the two B filters are arrayed in the row direction and each of the two B filters transmits the light of the wavelength band $H_B$. Therefore, the basic unit C23d is configured with the two B filters which are adjacent to each other in the row direction and the two G filters which are adjacent to each other in the row direction.

In the read unit C37d, the two B filters are arrayed in the column direction and each of the two B filters transmits the light of the wavelength band $H_B$. In the read unit C38d, the two G filters are arrayed in the column direction and each of the two G filters transmits the light of the wavelength band $H_G$. Therefore, the basic unit C24d is configured with the two G filters which are adjacent to each other in the row direction and the two B filters which are adjacent to each other in the row direction.

In the filter unit C11d, the read units C31d, C33d, C35d, and C37d are disposed in the odd-numbered rows, and the read units C32d, C34d, C36d, and C38d are disposed in the even-numbered rows.

Modified Example 3 of Second Embodiment

FIG. 26 is a schematic diagram illustrating an example of a configuration of a color filter according to Modified Example 3 of the second embodiment of the disclosure. A filter unit C11e according to the modified example is partitioned into basic units C21e to C24e which are four areas divided in 2 rows×2 columns. In addition, the basic units C21e to C24e are partitioned into read units C31e to C38e which are formed by dividing each basic unit in 1 row×2 columns. More specifically, the basic unit C21e is divided in 1 row×2 columns to include read units C31e and C32e, the basic unit C22e is divided in 1 row×2 columns to include read units C33e and C34e, the basic unit C23e is divided in 1 row×2 columns to include read units C35e and C36e, and the basic unit C24e is divided in 1 row×2 columns to include read units C37e and C38e.

As illustrated in FIG. 26, the filter unit C11e according to Modified Example 3 is configured with six (6/16) G filters transmitting the light of the wavelength band $H_G$, six (6/16) B filters transmitting the light of the wavelength band $H_B$, and four (4/16) R filters transmitting the light of the wavelength band $H_R$.

Each of the read units C31e and C32e includes two filters where each transmits light of the same wavelength band. More specifically, in the read unit C31e, the two G filters are arrayed in the column direction and each of the two G filters transmits the light of the wavelength band $H_G$. In the read unit C32e, the two B filters transmitting the light of the wavelength band $H_B$ are arrayed in the column direction and each of the two B filters transmits the light of the wavelength band $H_B$. Therefore, the basic unit C21e is configured with the two G filters which are adjacent to each other in the row direction and the two B filters which are adjacent to each other in the row direction.

In the read units C33e to C38e, similarly, each read unit includes two filters where each transmits light of the same wavelength band. More specifically, in the read unit C33e, the two R filters are arrayed in the row direction and each of the two R filters transmits the light of the wavelength band $H_R$. In the read unit C34e, the two G filters are arrayed in the row direction and each of the two G filters transmits the light of the wavelength band $H_G$. Therefore, the basic unit C22e is configured with the two R filters which are adjacent to each other in the row direction and the two G filters which are adjacent to each other in the row direction.

In the read unit C35e, the two R filters are arrayed in the row direction and each of the two R filters transmit the light of the wavelength band $H_R$. In the read unit C36e, the two B filters are arrayed in the row direction and each of the two B filters transmits the light of the wavelength band $H_B$. Therefore, the basic unit C23e is configured with the two R filters which are adjacent to each other in the row direction and the two B filters which are adjacent to each other in the row direction.

In the read unit C37e, the two B filters are arrayed in the row direction and each of the two B filters transmits the light of the wavelength band $H_B$. In the read unit C38e, the two G filters are arrayed in the row direction and each of the two G filters transmit the light of the wavelength band $H_G$. Therefore, the basic unit C24e is configured with the two G filters which are adjacent to each other in the row direction and the two B filters which are adjacent to each other in the row direction.

In the filter unit C11e, the read unit C31e, C33e, C35e, and C37e are disposed in the odd-numbered rows, and the read units C32e, C34e, C36e, and C38e are disposed in the even-numbered rows.

In addition, in the array in Modified Example 3, the G filters of the read unit C35d in Modified Example 2 are replaced with the R filters. Alternatively, the filters that are in the odd-numbered columns and satisfy the number of filters described above can be replaced with the R filters. For example, the B filters of the read unit C35c in Modified Example 1 may be replaced with the R filters.

In the filter units according to Modified Examples 1 to 3, similarly to the above-described second embodiment, it is possible to obtain the effect in that a clear image can be obtained in any one of the white light imaging mode and the narrow-band imaging mode.

In addition, in the above-described first embodiment, the signal process may be performed by using the color filter according to the second embodiment and Modified Examples 1 to 3.

Third Embodiment

Next, a third embodiment of the disclosure will be described. FIG. 27 is a schematic diagram illustrating an example of a configuration of a color filter according to the third embodiment of the disclosure. The same components as those of the above-described components are denoted by the same reference signs. In the first and second embodiments, the reading unit 244f reads the charges stored by the plurality of pixels arrayed in a lattice shape for every row (line). However, in the third embodiment, the reading unit reads the charges for every column.

In the color filter 244g according to the third embodiment, filter units C11f configured with sixteen filters aligned in a 4×4 matrix shape are disposed to be aligned two-dimensionally (in a matrix shape) according to the array of the pixel $P_{ij}$.

The filter unit C11f is partitioned into basic units C21f to C24f which are four areas divided in 2 rows×2 columns. In addition, the basic units C21f to C24f are partitioned into read units C31f to C38f which are formed by dividing each basic unit in 2 rows×1 column. More specifically, the basic unit C21f is divided in 2 rows×1 column to include read units C31f and C32f, the basic unit C22f is divided in 2 rows×1 column to include read units C33f and C34f, the basic unit C23f is divided in 2 rows×1 column to include read units C35f and C36f, and the basic unit C24f is divided in 2 rows×1 column to include read units C37f and C38f.

As illustrated in FIG. 27, the filter unit C11f according to the third embodiment is configured with eight (8/16) G filters transmitting the light of the wavelength band $H_G$, six (6/16) B filters transmitting the light of the wavelength band $H_B$, and two (2/16) R filters transmitting the light of the wavelength band $H_R$.

Each of the read units C31f and C32f includes two filters where each transmits light of the same wavelength band. More specifically, in the read unit C31f, the two G filters are arrayed in the column direction and each of the two G filters transmits the light of the wavelength band $H_G$. In the read unit C32f, the two B filters are arrayed in the column direction and each of the two B filters transmits the light of the wavelength band $H_B$. Therefore, the basic unit C21f is configured with the two G filters which are adjacent to each other in the column direction and the two B filters which are adjacent to each other in the column direction.

In the read units C33f to C38f, similarly, each read unit includes two filters where each transmits light of the same wavelength band. More specifically, in the read unit C33f, the two B filters are arrayed in the column direction and each of the two B filters transmits the light of the wavelength band $H_B$. In the read unit C34f, the two G filters are arrayed in the column direction and each of the two G filters transmits the light of the wavelength band $H_G$. Therefore, the basic unit C22f is configured with the two B filters which are adjacent to each other in the column direction and the two G filters which are adjacent to each other in the column direction.

In the read unit C35f, the two R filters are arrayed in the column direction and each of the two R filters transmits the light of the wavelength band $H_R$. In the read unit C36f, the two G filters are arrayed in the column direction and each of the two G filters transmits the light of the wavelength band $H_G$. Therefore, the basic unit C23f is configured with the two R filters which are adjacent to each other in the column direction and the two G filters which are adjacent to each other in the column direction.

In the read unit C37f, the two G filters are arrayed in the column direction and each of the two G filters transmits the light of the wavelength band $H_G$. In the read unit C38f, the two B filters are arrayed in the column direction and each of the two B filters transmits the light of the wavelength band $H_B$. Therefore, the basic unit C24f is configured with the two G filters which are adjacent to each other in the column direction and the two B filters which are adjacent to each other in the column direction.

In the filter unit C11f, the read units C31f, C33f, C35f, and C37f are disposed in the odd-numbered columns, and the read units C32f, C34f, C36f, and C38f are disposed in the even-numbered columns. Each basic unit is configured with the read units which are adjacent to each other in the direction (row direction) perpendicular to the array direction (column direction) of the filters of the read units.

In the third embodiment, for example, in case of performing the signal process according to the flowchart of FIG. 5, in step S101, the row direction is replaced with the column direction in reading, and the reading unit 244f performs the reading process on every column. The reading unit 244f outputs the charges stored by the plurality of pixels of the light receiving unit 244e as the imaging signal by collectively reading in each of the read units C31f to C38f. For example, the reading unit 244f sums up the charges stored by each of the $G_{11}$ pixel and the $G_{21}$ pixel corresponding to the read unit C31f and converts the summed charges into a voltage (summed value) to generate the imaging signal.

In addition, for example, in case of performing the signal process according to the flowchart of FIG. 16, in step S202, the odd-numbered rows are replaced with the odd-numbered columns in reading, and the reading unit 244f performs the reading process on the odd-numbered columns. Similarly, in step S205, the even-numbered rows are replaced with the even-numbered columns in reading, and the reading unit 244f performs the reading process on the even-numbered columns. The reading unit 244f reads the charges of the pixels of the read units disposed in any one column of the odd-numbered columns and the even-numbered columns under the control of the reading controller 244h.

According to the above-described third embodiment, similarly to the first and second embodiments, the filter unit C11f is configured with the eight G filters transmitting the light of the wavelength band $H_G$, the six B filters transmitting the light of the wavelength band $H_B$, and the two R filters transmitting the light of the wavelength band $H_R$, the extraction unit 402b is configured to generate the extraction image information of the extraction area configured with the four pixels corresponding to each of the basic unit C21f to C24f based on the color component information extracted by the color component separation unit 402a, and the image processing unit 402 is configured to generate the color image signal. Therefore, it is possible to obtain a clear image in any one of the white light imaging mode and the narrow-band imaging mode.

In the above-described first to third embodiments and modified examples, the filter units having the same array are disposed in a matrix shape. However, filter units having different arrays may be disposed in a matrix shape. For example, the filter unit C11 according to the first embodiment and the filter unit C11b according to the second embodiment are used, and the filter units C11 and C11b may be disposed in a matrix shape.

As described heretofore, a solid state image sensor, an endoscope, and an endoscope system according to the disclosure are useful to obtaining a clear image in any one of a white light imaging mode and a narrow-band imaging mode.

According to some embodiments, it is possible to obtain the effect in that a clear image can be obtained in any one of a white light imaging mode and a narrow-band imaging mode.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A solid state image sensor comprising:
   a light receiving unit where a plurality of photoelectric conversion elements storing charges according to a received light amount are arrayed in a lattice shape;
   a reading unit configured to read an imaging signal based on the charges stored by the light receiving unit; and
   a color filter including: red filters where each transmits light of a red wavelength band; green filters where each transmits light of a green wavelength band; and blue filters where each transmits light of a blue wavelength band, each of the red, green, and blue filters being disposed at a position corresponding to any one of the plurality of photoelectric conversion elements on a light receiving plane of the light receiving unit,
   wherein the color filter includes filter units where each includes the red, green, and blue filters arrayed in four rows and four columns, and the filter units are arrayed in a lattice shape,
   wherein the filter unit is set so that a total number of the green filters is six or more and eight or less, a total number of the blue filters is six or more and eight or less, a total number of the red filters is two or more and four or less, and a total number of the red, green, and blue filters is sixteen,
   the filter unit is partitioned into read units, each read unit includes two filters where each transmits light of the same wavelength band, and the two filters are adjacent to each other in one direction, and
   wherein the reading unit is configured to collectively read charges stored by two photoelectric conversion elements corresponding to the read unit.

2. The solid state image sensor according to claim 1, wherein in the read unit, the two filters where each transmits the light of the same wavelength band are adjacent to each other in a row direction, and
   wherein the reading unit is configured to read the charges stored by the photoelectric conversion elements in an odd-numbered row or an even-numbered row in accordance with an instruction from an outside.

3. The solid state image sensor according to claim 1, wherein in the read unit, the two filters where each transmits the light of the same wavelength band are adjacent to each other in a column direction, and
   wherein the reading unit is configured to read the charges stored by the photoelectric conversion elements in an odd-numbered column or an even-numbered column in accordance with an instruction from an outside.

4. The solid state image sensor according to claim 1, wherein each of the filter units has the same filter array.

5. An endoscope comprising the solid state image sensor according to claim 1 at a distal end of an insertion unit of the endoscope.

6. An endoscope system comprising:
   an endoscope provided with the solid state image sensor according to claim 1 at a distal end of an insertion unit of the endoscope;
   an illumination unit configured to emit white illumination light including light of red, green, and blue wavelength bands or narrow-band illumination light including: light of a narrow band included in the blue wavelength band; and light of a narrow band included in the green wavelength band; and
   an image processing unit connected to the endoscope and configured to generate an image signal for image display based on the imaging signal obtained from the endoscope,
   wherein the filter unit is partitioned into basic units, each basic unit where four filters corresponding to two read units adjacent to each other in a direction perpendicular to the one direction are arrayed in two rows and two columns, and
   wherein the image processing unit is configured: to generate image information of a single color component for every color component using the basic unit as a unit based on signal values of the photoelectric conversion elements corresponding to the read unit; and to generate an image signal for image display based on the generated image information.

7. The endoscope system according to claim 6,
wherein in the read unit, the two filters where each transmits the light of the same wavelength band are adjacent to each other in a row direction,
wherein the reading unit is configured to read the charges stored by the photoelectric conversion elements in an odd-numbered row or an even-numbered row according to illumination light emitted by the illumination unit, and
wherein the image processing unit is configured to generate the image information using an imaging signal based on the charges which are stored by the photoelectric conversion elements in the odd-numbered row or the even-numbered row and which are read by the reading unit.

8. The endoscope system according to claim 6,
wherein in the read unit, the two filters where each transmits the light of the same wavelength band are adjacent to each other in a column direction,
wherein the reading unit is configured to read the charges stored by the photoelectric conversion elements in an odd-numbered column or an even-numbered column according to illumination light emitted by the illumination unit, and
wherein the image processing unit is configured to generate the image information using the imaging signal based on the charges which are stored by the photoelectric conversion elements in the odd-numbered columns or the even-numbered columns and which are read by the reading unit.

* * * * *